US006235873B1

(12) United States Patent
Bromberg et al.

(10) Patent No.: US 6,235,873 B1
(45) Date of Patent: May 22, 2001

(54) CONSTITUTIVELY ACTIVE TRANSCRIPTION FACTORS AND THEIR USES FOR IDENTIFYING MODULATORS OF ACTIVITY INCLUDING DYSPROLIFERATIVE CELLULAR CHANGES

(75) Inventors: Jacqueline F. Bromberg; Melissa H. Wrzeszczynska; Yanxiang Zhao, all of New York; James E. Darnell, Jr., Larchmont, all of NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/364,970

(22) Filed: Jul. 31, 1999

(51) Int. Cl.[7] .......................... A61K 38/00; C07K 14/00; C08G 69/26; C07H 21/02

(52) U.S. Cl. ......................... 530/300; 530/350; 536/23.1; 435/320.1; 435/68.1

(58) Field of Search ..................................... 530/300, 350; 435/68.1, 69.1, 183, 320.1, 325; 536/23.1

(56) References Cited

PUBLICATIONS

Chen et al., 1998, Cell 93:827–39.
Garcia et al., 1998, J. Biomed. Sci 5:79–85.
Yu et al., 1995, Science 269:81–3.
Catlett–Falcone, 1999,Immunity 10:105–15.
Onishi et al., 1998, Mol. Cell Biol. 18:3871–9.

*Primary Examiner*—John S. Brusca
*Assistant Examiner*—Stephen Siu
(74) *Attorney, Agent, or Firm*—Klauber & Jackson

(57) ABSTRACT

The invention is directed to constitutively active Stat proteins and methods for their preparation. The modified Stat proteins have at least one cysteine residue which may interact with the corresponding cysteine residue on another modified Stat protein to form a dimer. The constitutively active Stat proteins are capable of binding to DNA and activating transcription in the absence of tyrosine phosphorylation. Cell lines expressing the modified Stat protein exhibit a transformed phenotype and are capable of forming tumors in nude mice. Methods are describe utilizing the modified Stat proteins of the invention in the absence and presence of tyrosine phosphorylation in identifying agents capable of modulating Stat protein dimerization, transcriptional activity, and cellular transformation in vitro and in vivo. The invention is also directed to polynucleotides encoding modified, constitutively active Stat proteins.

51 Claims, 6 Drawing Sheets

FIG.1A
FIG.1B
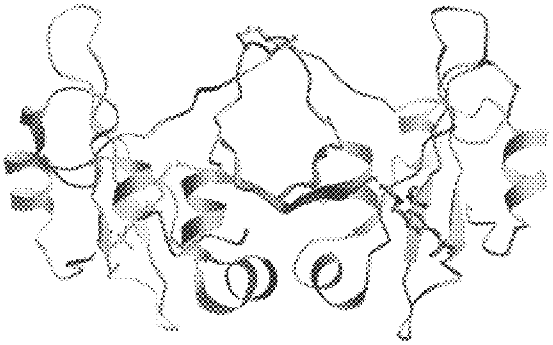
FIG. 1C
C-Terminal Loops
| | 655 ... 676 |
|---|---|
| **STAT3** | GYKIMDATNILVSPLVYLYPDI |
| STAT1 | NYKVMAAENIPENPLKYLYPNI |
| STAT4 | DYKVIMAENIPENPLKYLYPDI |
| STAT2 | HYQLLTEENIPENPLRFLYPRI |
| STAT5 | DLNY----------LIYVFPDR |
| STAT6 | DLAQ----------LKNLYPKK |

CONSTITUTIVELY ACTIVE TRANSCRIPTION FACTORS AND THEIR USES FOR IDENTIFYING MODULATORS OF ACTIVITY INCLUDING DYSPROLIFERATIVE CELLULAR CHANGES

GOVERNMENTAL SUPPORT

The research leading to the present invention was supported, in part, by a grant from the National Institutes of Health, National Cancer Institute, Grant Nos. R29CA70897 and RO1CA75503. Accordingly, the Government may have certain rights in the invention.

FIELD OF THE INVENTION

The present invention is directed to modified Stat proteins that in the absence of tyrosine phosphorylation are capable of constitutive dimerization, transcriptional activation, and induction in transfected cells of cellular transformation and tumorigenesis, as well as their utility in identifying agents capable of modulating cellular transformation and tumorigenesis.

BACKGROUND OF THE INVENTION

Stat (Signal Transducers and Activators of Transcription) proteins are latent transcription factors that become activated by phosphorylation on a single tyrosine (near residue 700), typically in response to extracellular ligands (Darnell, 1997; Stark et al., 1998; U.S. application Ser. Nos. 08/212,185, filed Mar. 11, 1994; Ser. No. 09/087,465, filed May 29, 1998; Ser. No. 08/951,130, filed Oct. 15, 1997; Ser. No. 09/012,710, filed Jan. 23, 1998; Ser. No. 08/820,754, filed Mar. 19, 1997; and U.S. Pat. No. 5,716,622; all of the foregoing incorporated herein by reference in their entireties). More than 40 different polypeptide ligands cause Stat phosphorylation through either cytokine receptors plus associated Jak kinases or growth factors (e.g. EGF, PDGF, CSF-1) acting through intrinsic receptor tyrosine kinases. An active Stat dimer is formed via the reciprocal interactions between the SH2 domain of the monomer and the phosphorylated tyrosine of the other (Chen et al., 1998). The dimers accumulate in the nucleus, recognize specific DNA elements and activate transcription. The Stat proteins are subsequently inactivated by tyrosine dephosphorylation and return to the cytoplasm (Haspel et al., 1996).

Ligand dependent activation of the Stats is often associated with differentiation and/or growth regulation while constitutive activation of Stats (i.e. activation without known requirements of extracellular polypeptides) is often associated with growth dysregulation. For example, the development of the antiviral state or growth restraint secondary to either IFN-α of IFN-γ treatment requires transcriptionally competent Stat1 (Bromberg et al., 1996; Horvath and Darnell, 1996) and mice lacking Stat1 form chemically induced tumors of the skin more easily than wild-type animals (Kaplan et el., 1998). Various stages of lymphocyte or monocyte development depend on Stats 3, 4 and 6 (Kaplan et al., 1996; Takeda et al., 1996; Thierfelder et al., 1996; Takeda et al., 1998; Takeda et al., 1999); development of breast epithelium requires Stat5A (Liu et al., 1997; Teglund et al., 1998), and proper male growth hormone response demands Stat5B (Udy et al, 1997; Teglund et al., 1998). A growing number of tumor-derived cell lines as well as samples from human cancers are reported to contain constitutively activated Stat proteins, very frequently Stat3 (Garcia and Jove, 1998). For example, all src transformed cell lines exhibit constitutively activated Stat3 (Yu et al, 1995). Moreover, dominant negative Stat3 suppresses src transformation without having any effect on ras transformation (Bromberg et al., 1998; Turkson et al., 1998). Cell lines from multiple myelomas that have become growth factor independent require constitutively active Stat3 to protect against apoptosis (Catlett-Falcone et al., 1999). A high proportion of head and neck cancers (often of squamous cell origin) have constitutively active Stat3, most likely secondary to aberrant EGF receptor signaling (Grandis et al., 1998) and dominant negative Stat3 slows the growth of cell lines developed from these cancers.

Oncogenes were first defined as viral or mutated cellular genes that could confer a transformed phenotype to cultured cells (Lodish et al., 1995). When oncogenes were characterized at the molecular level, many were found to be constitutively activated. One constitutively activated Stat molecule has been described. Amino acid changes in two separate domains of Stat5 results in constitutive activation and obviates the need for IL-3 in the growth of BaF3 cells (Onishi et al., 1998). However, the amino acids that are changed in the Stat5 molecule (H-$R^{299}$ and S-$F^{711}$) are not conserved between Stat5 and Stat3.

It is toward the development of a dimerizable and constitutively active Stat protein particularly in the absence of tyrosine phosphorylation and its utility in investigating the role of the active protein in transcription and inducing cell transformation, and the effects of modulators thereon, that the present invention is directed.

The citation of any reference herein should not be construed as an admission that such reference is available as "Prior Art" to the instant application.

SUMMARY OF THE INVENTION

In its broadest aspect, the present invention is directed to modified Stat proteins capable of constitutively dimerizing and binding to DNA in the absence of tyrosine phosphorylation. The modified Stat proteins have at least one cysteine residue provided in the Stat protein which is capable of interacting with the same cysteine residue on a second modified Stat protein, forming a dimer. Non-limiting examples of Stat proteins that may be so modified include Stat1 (SEQ ID NO:1), Stat2 (SEQ ID NO:2), Stat3 (SEQ ID NO:3), Stat4 (SEQ ID NO:4), Stat5 and Stat6. The first cysteine may be provided in a conserved domain of the Stat protein; for example, the C-terminal loop of the SH2 domain. Suitable positions include but are not limited to position 656 or 658 Stat1; position 706 or 707 of Stat1; position 653 or 655 of Stat2; position 725 or 726 of Stat 2; position 710 or 711 of Stat 3; position 662 or 664 of Stat3; position 651 or 653 of Stat4; position 699 or 700 of Stat 4; position 715 or 716 of Stat5; or position 697 or 698 of Stat6. In a further aspect of the invention, a second cysteine is provided in the modified Stat protein, for example, both aforementioned positions in the Stat molecules, i.e., position 656 and 658 of Stat1; position 706 and 707 of Stat1; position 653 and 655 of Stat2; position 725 and 726 of Stat 2; position 710 and 711 of Stat 3; position 662 and 664 of Stat3; position 651 and 653 of Stat4; position 699 and 700 of Stat 4; position 715 and 716 of Stat5; or position 697 and 698 of Stat6. In a preferred embodiment of the invention, the modified Stat protein is Stat3, wherein position 662 is C, and position 664 is C (SEQ ID NO:5). In a still further aspect, the modified Stat protein may have a third or a third and fourth cysteine residue.

In a further aspect of the invention, the modified Stat protein further comprises an epitope tag, for example, FLAG.

The invention is also directed to the polynucleotide sequences encoding the aforementioned modified Stat proteins, including those with an epitope tag.

In another broad aspect of the present invention, a method is provided for preparing a modified Stat protein capable of constitutively dimerizing and binding to DNA in the absence of phosphorylation. The method involves introducing in a Stat protein at least one cysteine; for example, by site-directed mutagenesis, wherein the cysteine of a first modified Stat protein molecule is capable of interacting with the same residue of a second modified Stat protein, forming a dimer. Non-limiting examples of suitable Stat proteins include Stat1 (SEQ ID NO:1), Stat2 (SEQ ID NO:2), Stat3 (SEQ ID NO:3), and Stat4 (SEQ ID NO:4). The first cysteine residue may be introduced into a conserved domain of said Stat protein, for example, the C-terminal loop of the SH2 domain. By way of non-limiting example, a cysteine residue introduced into the modified Stat protein is capable of interacting with and promoting dimer formation with the introduced cysteine residue on a second modified Stat protein. Examples of suitable positions include but are not limited to position 656 or 658 of Stat1; position 706 or 707 Stat1; position 653 or 655 of Stat2; 725 or 726 of Stat 2; position 710 or 711 of Stat 3; position 662 or 664 of Stat3; position 651 or 653 of Stat4; 699 or 700 of Stat 4; position 715 or 716 of Stat5; or position 697 or 698 of Stat6.

Any technique for mutagenesis known in the art can be used for providing the residues as described above, including but not limited to, in vitro site-directed mutagenesis.

In a preferred embodiment, a second cysteine residue may be introduced into said modified Stat protein, for example, both positions in the aforementioned list of examples, i.e., positions 656 and 658 of Stat1; positions 706 and 707 of Stat1; positions 653 and 655 of Stat2; positions 725 and 726 of Stat 2; positions 710 and 711 of Stat 3; positions 662 and 664 of Stat3; positions 651 and 653 of Stat4; positions 699 and 700 of Stat 4; positions 715 and 716 of Stat5; or positions 697 and 698 of Stat6. In a preferred embodiment of a modified Stat protein prepared by the aforementioned methods is Stat3 wherein A 662 is changed to C and N 664 is changed to C (SEQ ID NO:5). The modified Stat protein may further comprise an epitope tag, for example, FLAG. In a still further aspect, the Stat protein may be modified to have a third or a third and a fourth cysteine.

In another broad aspect, the present invention is directed to a method for identifying an agent which is capable of modulating the dimerization of a Stat protein in the absence of tyrosine phosphorylation, comprising the steps of (a) providing a constitutively active Stat protein producing cell line; (b) introducing to a sample of cells from the cell line an agent suspected of modulating dimerization of the constitutively active Stat protein; and (c) examining the cells for a consequence of Stat protein dimerization by the agent. Non-limiting examples of means for identifying consequences of Stat protein dimerization include measuring the extend of DNA binding in the cells by said Stat protein, oncogenesis in the cells as determined by morphological changes; colony formation by the cells, expression in the cells of a reported gene in the cyclin D1 promoter; increased nuclear presence of Stat protein, development of an antiviral state, growth restraint secondary to IFN-α or IFN-γ treatment, and apoptosis of the cells. In a further embodiment, the agent may be capable of modulating dimerization of a Stat protein in the presence of tyrosine phosphorylation, wherein the aforementioned method is carried out in the presence of a means for inducing tyrosine phosphorylation, such as by transfecting the cells with v-src or treating said cells with a combination of IL-6 and soluble IL-6 receptor. The aforementioned methods may also be carried out in a cell-free system, wherein the effects of the agent on Stat dimerization may be monitored; for example, by measuring the extent of DNA binding by said Stat protein, or transcription of a construct of a reporter gene with a Stat DNA target.

In another aspect of the invention, a method is provided for identifying cells transformed by a constitutively active Stat protein comprising measuring the level of cyclin D1 mRNA in the cells, comparing the level to cyclin D1 mRNA levels in normal cells, and identifying cells transformed by the constitutively active Stat protein as those with a cyclin D1 message RNA level greater than normal.

In yet a further broad aspect of the present invention, methods are provided for identifying an agent capable of modulating transcriptional activation of a reporter gene with a Stat DNA binding site comprising the steps of: (1) transfecting a reporter gene with a Stat DNA binding site into a cell line; (2) transfecting the cell line with a constitutively active Stat protein; and (3) correlating a change in the extent of expression of the reporter gene as a consequence of the presence of the agent with the activity of the agent. By way of non-limiting examples, the reported gene may be a m67-luciferase reporter gene construct or a cyclin D1-luciferase reporter gene construct. The method may additionally afford means for inducing tyrosine phosphorylation in said cell line, such as by transfecting said cells with v-src or treating said cells with a combination of IL-6 and soluble IL-6 receptor.

In a further aspect of the invention, a method is provided for identifying an agent capable of modulating the interactions between a constitutively activate Stat protein dimer and its target DNA sequence, comprising the steps of (a) providing a constitutively dimerizable Stat protein as described hereinabove; (b) providing a target DNA sequence; (c) introducing an agent to a mixture of the foregoing; (d) determining the extend of association between the Stat protein and the target DNA; and (e) correlating the association with the ability of the agent to modulate the interaction. The Stat protein may be prepared from a nuclear extract of a cell transfected with a modified Stat protein. The agent may interfere with or promote the interaction.

In yet a further aspect, the present invention is directed to a method for the identification of an agent capable of modulating cell growth or proliferation which is mediated by the interaction between a Stat protein and DNA in the absence of tyrosine phosphorylation, comprising the steps of: (a) providing a constitutively active Stat protein producing cell line; (b) introducing to a sample of cells from the cell line an agent suspected of modulating the interaction; and (c) examining the cells for a consequence of Stat protein interaction by the agent. Non-limiting examples of methods for identifying the consequence of Stat protein interaction with DNA include: the extent of DNA binding in the cells by the Stat protein, oncogenesis in the cells as determined by morphological changes; colony formation by the cells, expression in the cells of a reporter gene in the cyclin D1 promoter; increased nuclear presence of Stat protein, development of an antiviral state, growth restraint secondary to IFN-γ or IFN-α treatment, and apoptosis of the cells. The method may also be used to identify an agent capable of modulating dimerization of a Stat protein in the presence of tyrosine phosphorylation by carrying out the above method in the presence of a means for inducing tyrosine phosphorylation; for example, by transfecting said cells with v-scr and treating said cells with a combination of IL-6 and soluble IL-6 receptor. Preferably, the method is used to identify agents capable of blocking transformation of cells.

In a further aspect, the present invention is directed to a cell line expressing a modified Stat protein as described hereinabove. In yet a further aspect, the cell line is capable of forming tumors in nude mice.

In still a further aspect, a method is described for identifying an agent capable of modulating the tumorigenesis by cells expressing a constitutively active Stat protein, comprising the steps of (a) implanting cells expressing a constitutively active Stat protein in nude mice; (b) treating a mouse of step (a) with the agent; and (c) comparing the growth of a tumor from the cells in mice treated with said agent to mice not treated with said agent to identify the agent as capable of modulating tumorigenesis. In a preferred embodiment, the cells express a Stat protein as described.

In another aspect, the present invention provides a method for identifying an agent capable of inhibiting cellular transformation comprising exposing a transformed cell line expressing a modified Stat protein as described hereinabove to an agent suspected of inhibiting cellular transformation, followed by determining the effect of the agent on cellular transformation.

The aforementioned methods may be applied to procedures for screening agents for activity in modulating transcriptional activation by the modified Stat proteins of the present invention. For example, a method for identifying an agent which is capable of modulating the dimerization of a Stat protein in the absence of tyrosine phosphorylation, may be carried out by following the steps of (a) providing a constitutively active Stat protein producing cell line; (b) introducing to a sample of cells from the cell line an agent suspected of modulating dimerization of the constitutively active Stat protein; and (c) examining the cells for a consequence of Stat protein dimerization by the agent. The constitutively active Stat protein is that described hereinabove. Examples of means for identifying consequences of Stat protein dimerization include measuring the extend of DNA binding in the cells by said Stat protein, oncogenesis in the cells as determined by morphological changes; colony formation by the cells, expression in the cells of a reporter gene in the cyclin d1 promoter; increased nuclear presence of Stat protein, development of an antiviral state, growth restraint secondary to IFN-γ or IFN-α treatment, and apoptosis of the cells. These means are described in the examples below. In a further embodiment, the agent may be capable of modulating dimerization of a Stat protein in the presence of tyrosine phosphorylation, wherein the aforementioned method is carried out in the presence of a means for inducing tyrosine phosphorylation, such as by transfecting the cells with v-src or treating said cells with a combination of IL-6 and soluble IL-6 receptor. The aforementioned methods may also be carried out in a cell-free system, wherein the effects of the agent on Stat dimerization may be monitored for example by measuring the extent of DNA binding by said Stat protein, or by monitoring transcription of a construct of a reporter gene with a Stat DNA target.

Methods are provided herein for identifying an agent capable of modulating transcriptional activation of a reporter gene with a Stat DNA binding site comprising the steps of: (1) transfecting a reporter gene with a Stat DNA binding site into a cell line; (2) transfecting the cell line with a constitutively active Stat protein; and (3) correlating a change in the extent of expression of the reporter gene as a consequence of the presence of the agent with the activity of the agent. By way of non-limiting examples, the reported gene may be a m67-luciferase reporter gene construct or a cyclin D1-luciferase reporter gene construct. The method may additionally comprise means for inducing tyrosine phosphorylation in said cell line, such as by transfecting said cells with v-src or treating said cells with a combination of IL-6 and soluble IL-6 receptor.

In a further embodiment, a method is provided for identifying an agent capable of modulating the interactions between a constitutively activate Stat protein dimer and its target DNA sequence, comprising the steps of (a) providing a constitutively dimerizable Stat protein as described hereinabove; (b) providing a target DNA sequence; (c) introducing an agent to a mixture of the foregoing; (d) determining the extent of association between the Stat protein and the target DNA; and (e) correlating the association with the ability of the agent to modulate the interaction. The Stat protein may be prepared from a nuclear extract of a cell transfected with a modified Stat protein. The agent may interfere with or promote the interaction. Thus, agonists or antagonists of the interaction may be identified, and used for the aforementioned purposes relating, for example, to the treatment or prevention of dysproliferative disease, and the immortalization of cell lines.

The present invention is also directed to a method for the identification of an agent capable of modulating cell growth or proliferation which is mediated by the interaction between a Stat protein and DNA in the absence of tyrosine phosphorylation, comprising the steps of: (a) providing a constitutively active Stat protein producing cell line; (b) introducing to a sample of cells from the cell line an agent suspected of modulating the interaction; and (b) examining the cells for a consequence of Stat protein interaction by the agent. Examples of measuring these effects are as described above. The method may also be used to identify an agent capably of modulating dimerization of a Stat protein in the presence of tyrosine phosphorylation by carrying out the above method in the presence of a means for inducing tyrosine phosphorylation; for example, by transfecting said cells with v-src and treating said cells with a combination of IL-6 and soluble IL-6 receptor. Preferably, the method is used to identify agents capable of blocking transformation of cells.

The present invention is directed to a cell line expressing a modified Stat protein as described hereinabove. As described herein, cell lines expressing a constitutively active Stat protein include 3Y-1-Stat3-C and NIH3T3-Stat3-C. Other cells lines may be accordingly prepared following the methods described herein. Such cell lines may be capable of forming tumors in nude mice.

A method is described herein for identifying an agent capable of modulating the tumorigenesis by cells expressing a constitutively active Stat protein comprising the steps of (a) implanting cells expressing a constitutively active Stat protein in nude mice; (b) treating a mouse of step (a) with the agent; and (c) comparing the growth of a tumor from the cells in mice treated with said agent to mice not treated with said agent to identify the agent as capable of modulating tumorigenesis. In a preferred embodiment, the cells express a Stat protein as described above.

The present invention also provides a method for identifying an agent capable of inhibiting cellular transformation comprising exposing a transformed cell line expressing a modified Stat protein as described hereinabove to an agent suspected of inhibiting cellular transformation, followed by determining the effect of the agent on cellular transformation.

These and other aspects of the present invention will be better appreciated by reference to the following drawings and Detailed Description.

BRIEF DESCRIPTION OF THE DRAWINGS

FIGS. 1A–1C depict the crystal structure of Stat1 and Cysteine Bridging through the C-Terminal Loop. (A) The C-terminal loops within the SH2 domain of a Stat1 homodimer approach 6 Å of one another. The crystal structures of Stat1 and Stat3 in this portion of the molecule are virtually superimposable. (B) A662C and N664C mutations of the Stat3 molecule allow for disulfide bridges to form in the C-terminal loops of the —SH2 domains of two monomers. (C) A662 and N664 are conserved between Stat3, Stat1 and Stat4 in the C-terminal loop of the SH2 domain.

DETAILED DESCRIPTION OF THE INVENTION

Figure 2A:
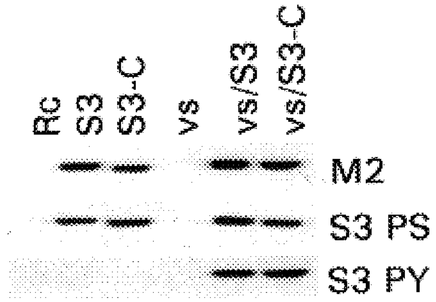
FIGS. 2A–2D depict a biochemical analysis of Stat3-C. (A) Western blots from 293T derived extracts. 293T cells were transiently transfected with RcCMV(Rc), Stat3(S3), Stat3-C(S3-C), v-src (vs), v-src with Stat3 (vs/S3), or v-src with Stat3-C (vs/S3-C). Twenty-four hrs later nuclear extracts were made from the transfected cells, separated by SDS-PAGE and transferred to nitrocellulose membranes. The top blot was probed with anti-FLAG M2 antibody (M2) (in this experiment both Stat3 and Stat3-C are FLAG-tagged at their COOH-terminus), the middle blot with anti-phosphoserine Stat3 antibody (S3 PS) and the bottom blot with anti-phosphotyrosine Stat3 antibody (S3 PY). (B) EMSA. The same extracts were incubated with a $^{32}$P-labeled high affinity binding site for Stat3 and resolved on a non-denaturing polyacrylamide gel. 1: RcCMV, 2: RcCMV/M2, 3: Stat3, 4: Stat3/M2, 5: Stat3-C, 6: Stat3-C/M2, 7: vsrc, 8: vsrc/M2, 9: Stat3/vsrc, 10: Stat3/vsrc/M2, 11: Stat3-C/vsrc, 12: Stat3-C/vsrc/M2, 13: v-src transformed cells, 14: v-src transformed cells/M2. Alternate samples were incubated with anti-FLAG M2 antibody as indicated. V-scr transformed cells containing tyrosine phosphorylated wild-type Stat3 protein (non-FLAG tagged), was not affected by M2 antibody. (C) Competition with β-mercaptoethanol. Extracts containing Stat3-C (S3-C) or tyrosine phosphorylated Stat3 (S3/vs, v-src) were incubated with increasing amounts of β-mercaptoethanol (β-SH nM) and subsequently resolved on a non-denaturing polyacrylamide gel. (D) Off rate of Stat3-C and Stat3 for m67. (i) Extracts containing Stat3-C (S3-C) or tyrosine phosphorylated Stat3 (S3/vs) (approximately equal total protein by western blot) (ii) were incubated with 2 ng or 10 ng of non-radiolabeled m67 than 1 ng of radiolabeled m67 and resolved on a non-denaturing polyacrylamide gel. (iii) These same amounts of extract were incubated with 1 ng of radiolabeled m67 for 5 mins followed by addition of a 100-fold greater amount of non-radiolabeled m67. Aliquots were removed before addition and at indicated intervals after addition of unlabeled oligonucleotides and loaded onto a continuously running non-denaturing polyacrylamide gel.

Stat proteins are latent transcription factors that require cytoplasmic tyrosine phosphorylation to become active as dimeric DNA binding proteins. The Stats mediate cytokine and growth factor directed transcription, with subsequent regulation of differentiation and growth. In a number of human cancers and transformed cell lines, Stat3 is active as a tyrosine phosphorylated DNA binding protein (constitutively activated) without a known activation mechanism. In a number of these cases, active Stat3 is either required for transformation, enhances transformation or blocks apoptosis. Stat proteins are described in application Ser. No. 08/212,185, incorporated herein by reference, as well as in several articles in the cited references herein, which are also incorporated by reference.

The inventors herein have made the discovery of modified Stat proteins capable of spontaneously dimerizing and binding to its target DNA in the absence of tyrosine phosphorylation. Such modified Stat proteins, also referred to as a constitutively active or activated Stat protein, may be prepared by modifying certain amino acid residues of the native Stat protein in a region of close association in the Stat dimer consequent to phosphorylation, to promote the association of the modified Stat proteins to form a dimer in the absence of phosphorylation. By way of non-limiting example, substitution of two residues, at positions 662 and 664, within the C-terminal loop of the SH2 domain of Stat3 with cysteine residues produces a molecule that dimerizes spontaneously (i.e. without tyrosine phosphorylation), binds to a Stat3 DNA binding element and directs transcription from a promoter containing this element. A further example is a modified Stat1 molecule with the residues at positions 656 and 658 changed to cysteines. Referred to herein as constitutively active Stat or Stat3-C, expression of this molecule by immortalized fibroblasts results in cellular transformation as determined by colony formation in soft agar; furthermore, stable cell lines expressing Stat3-C form tumors in nude mice. These experiments provide evidence that a constitutively activated Stat3 molecule by itself can mediate cellular transformation, and focus attention on the importance of constitutive Stat3 activation in human tumors.

As will be described in more detail below, the modified Stat proteins of the present invention capable in the absence of tyrosine phosphorylation of dimerization and subsequent DNA binding, and methods for their preparation, provide modified Stat proteins useful for a variety of methods for identifying the role of Stat proteins and Stat protein dimerization in gene activation, cell growth, differentiation, transformation, and tumorigenesis, and in particular facilitates the identification of agents capable of modulating the interaction between active Stat proteins and their DNA targets. One goal of these methods is to identify agents that can block cellular transformation which leads to tumorigenesis. Such agents are useful in the treatment and prevention of dysproliferative diseases, such as cancer and psoriasis. In contrast, agents capable of promoting the association of Stat proteins with DNA targets and activating cell cycle genes are useful in, for example, mimicking cell stimulation by cytokines.

The Stat proteins referred to herein include Stat proteins with conserved sequences, by way of non-limiting example Stat1 (SEQ ID NO:1), Stat2 (SEQ ID NO:2), Stat3 (SEQ ID NO:3), and Stat4 (SEQ ID NO:4). Stat1 includes Stat1α and Stat1β. While the sequences shown here are those of human Stat1 and Stat2, and murine Stat3 and Stat4, the present invention embraces Stat proteins of all species, for example, human, mammalian such as murine, sea urchin, Drosophila spp., *Caenorhabditis elegans*, and Dictyostelium spp. The appropriate Stat protein and species of origin may be selected for carrying out the appropriate procedure; for example, an in-vitro screen may utilize a particular murine Stat in a murine cell-based system; human Stat may be appropriate for screening compounds that interfere with tumorigenesis of a particular human cancer. A modified Stat protein derived from one species may be engineered into a cell of another species to provide, for example, a suitable system for a screening procedure. The skilled artisan will be aware of appropriate experimental design and the selection and combination of the appropriate components based upon the teachings herein. The present invention also embraces the various allelic variants of the Stat proteins, such as, by way of non-limiting example, that of human Stat3 described in EP0906953, incorporated herein by reference.

In the studies disclosed herein, modification of at least one amino acid residue in the Stat molecule was performed in order to promote the dimerization and subsequent binding to target DNA without the need for tyrosine phosphorylation. In the Examples provided below, the introduction of cysteine residues in place of other residues was performed to promote the formation of Stat dimers by disulfide bond formation between the cysteines. Identification of sites for modification of a Stat protein likely to render it constitutively active were based on the crystal structures of Stat1 and Stat3, which are virtually superimposable. The DNA bound dimers make protein-protein contact only in the SH2 domains. The phosphotyrosine (residues 701 in Stat1 and 705 in Stat3) of one monomer is extended on a ~17 amino acid unstructed tether to bind to the R602 (Stat1) or R608 (Stat3) in the SH2 pocket of its partner; a reciprocal interaction completes the contacts between the two monomers. In both the Stat1 or Stat3 homodimer there are loops just N-terminal to the —COOH end of the SH2 domain that are in close proximity to one another. By substituting cysteine residues for A662 and N664 of the Stat3 molecule, disulfide bonds may form between Stat3 monomers and render the molecule capable of dimerizing without a phosphate on Y705. Other residues in close proximity in this and other Stat molecules includes position 656 or 658 of Stat1; 706 or 707 of Stat1; position 653 or 655 of Stat2; position 725 or 726 of Stat2; position 710 or 711 of Stat 3; position 651 or 653 of Stat4; position 699 or 700 of Stat 4; position 715 or 716 of Stat5; or position 697 or 698 of Stat6. While not wishing to be bound by theory and under no obligation to disclose a theory of how the modified Stat proteins of the present invention dimerize, the one or both cysteines on one Stat molecule may form one or two disulfide bonds with the corresponding or the contralateral cysteine(s) on the other Stat protein. Such a molecule, herein termed Stat3-C, was made by site-directed mutagenesis of wild-type Stat3 to which an epitope tag (FLAG) was also appended for ease in following the molecule in cells. Similar procedures were used to prepare a modified Stat1 molecule with cysteines at positions 656 and 658. These and other methods are known to the skilled artisan, such as described in Hutchinson, C., et al., 1978, J. Biol. Chem. 253:6551; Zoller and Smith, 1984, DNA 3:479–488; and Oliphant et al., 1986, Gene 44:177; Hutchinson et al., 1986, Proc. Natl. Acad. Sci. U.S.A. 83:710. Other means for preparation of the modified Stat protein are embraced herein, including but not limited to solid phase synthesis. As notes above, at least one modification of the Stat protein is required to promote dimerization in the absence of tyrosine phosphorylation; additional modifications of other residues in the associating regions of the Stat protein, as well as the types of residues provided and their affinities of association, will regulate the extent of dimer formation. The present invention provides for a modified Stat protein capable of forming dimers and binding to DNA. As notes in the examples below, the modified Stat3-C protein with two cysteine residues is believed to associate through one or more disulfide bonds as shown by the sensitivity of dimer formation to a reducing agent.

By way of particular but non-limiting examples of the changes of one or two amino acids in Stat molecules to prepare the modified, constitutively active Stat molecules of the present invention, one or both of the following pairs of amino acids in each of the Stat molecules may be changed to cysteine. Furthermore, additional changes beyond two are embraced herein, such as both residues in a pair at one location in a Stat molecule, and one or both residues in a second associating pair in another region of the same molecule. Thus, the modified Stat protein may have three or four cysteine residues. The following list includes examples of such residue changes to cysteine [shown in format of (naturally-occurring reside) (position) (cysteine)]: A656C or N658C of Stat1; L706C or I707C of Stat1; E653C or N655C of Stat2; L725C or G726C of Stat 2; F710C or I711C of Stat3; A662C or N664C of Stat3; A651C or N653C of Stat4; F699C or I700C of Stat 4; G715C or S716C of Stat5; or S697C or H698C of Stat6. A modified Stat protein of the invention may have one or both of the foregoing cysteines. In a further example, a modified Stat protein may have both pairs modified, such as positions 656 and 658 of Stat1; positions 706 and 707 of Stat1; positions 653 and 655 of Stat2; positions 725 and 726 of Stat 2; positions 710 and 711 of Stat 3; positions 662 and 664 of Stat3; positions 651 and 653 of Stat4; positions 699 and 700 of Stat 4; positions 715 and 716 of Stat5; or positions 697 and 698 of Stat6. In a further embodiment, a modified Stat1 protein may have one pair and a third cysteine, such as positions 656 and 658 and one of position 706 or 707, alternatively, positions 706 and 707 and one of positions 656 or 658. Another example is positions 651 and 653 and position 699 or 700 of Stat4; alternately, positions 699 and 700 and one of position 651 or 653. A further example is positions 653 and 655 of Stat2 and position 725 or 726; alternatively, positions 725 and 726 and one of position 653 or 655. In the instance of Stat3, positions 662 and 664 may be cysteines, together with one of position 710 or 711; alternatively, positions 710 and 711 may be cysteine along with one of position 662 or 664. In a further embodiment, the modified Stat proteins may have two pairs of amino acids changed to cysteines; for example, in Stat 1, positions 656, 658, 706 and 707; in Stat 2, 653, 655, 725 and 726; in Stat3, positions 662, 664, 710 and 711; and in Stat4, positions 651, 653, 699 and 700. These examples are provided for illustrative purposes only; the skilled artisan in taking account of the closely associating regions of the Stat proteins in dimers will readily determine the appropriate locations of residue modification to provide cysteine residues to promote dimerization without the requirement for tyrosine phosphorylation. The requirement for one, two, three or four cysteine residues may be determined readily by the methods described herein.

The invention is also directed to polynucleotide sequences encoding the aforementioned modified Stat proteins capable of dimerization in the absence of tyrosine phosphorylation. Such polynucleotide sequences may also include an epitope tag. Examples of such polynucleotide sequences include but are not limited to the sequences encoding Stat proteins with at least one of the following residue changed to cysteine [shown in format of (naturally-occurring residue) (position) (cysteine)]: A656C or N658C of Stat1; L706C or I707C of Stat1; E653C or N655C of Stat2; L725C or G726C of Stat 2; F710C or I711C of Stat 3; A662C or N664C of Stat3; A651C or N653C of Stat4; F699C or I700C of Stat 4; G715C or S716C of Stat5; or S697C or H698C of Stat6. The polynucleotide encoding a modified Stat protein of the invention may have one or both of the foregoing cysteines: by way of further example, the polynucleotide of the invention encodes a modified Stat protein with both residues modified, such as positions 656 and 658 of Stat1 (SEQ ID NO: 10); positions 706 and 707 of Stat1; positions 653 and 655 of Stat2; positions 725 and 726 of Stat 2; positions 710 and 711 of Stat 3; positions 662 and 664 of Stat3 (SEQ ID NO:9); positions 651 and 653 of Stat4; positions 699 and 700 of Stat 4; positions 715 and 716 of Stat5; or positions 697 and 698 of Stat6. In a further embodiment, polynucleotides encode a modified Stat protein may have one pair and a third cysteine, such as positions 656 and 658 and one of position 706 or 707, alternatively, positions 706 and 707 and one of positions 656 or 658. Another example is positions 651 and 653 and position 699 or 700 of Stat4; alternately, positions 699 and 700 and one of position 651 or 653. As mentioned above, any of these polynucleotide sequences with from one to four residues modified to cysteine may have an epitope tag, such as FLAG.

Analysis of the Stat3-C molecules prepared as described above was performed in cells transiently transfection with the modified Stat protein and confirmed the ability of the modified Stat protein to bind DNA and exhibit transcriptional activation. As shown in the Examples below, Western blot analysis of nuclear extracts from serum grown cells transfected with Stat3-C revealed production of a protein that was serine phosphorylated but not tyrosine phosphorylated. Tyrosine phosphorylation could be provided by co-transfected with the tyrosine kinase v-src. Importantly, without v-src there was no binding of wild-type Stat3 but there was constitutive binding of Stat3-C to DNA, demonstrating its ability to bind in the absence of tyrosine phosphorylation. In the cells co-transfected with v-src, the now tyrosine phosphorylated wild-type Stat3 bound to DNA, as expected, yet there was increased binding to DNA in extracts from cells transfected with Stat3-C plus v-src. Additional studies on the Stat1-C molecule are provided in the Examples below. The methods of the present invention may be performed in the absence of tyrosine phosphorylation but may optionally be performed with tyrosine phosphorylation.

The compositions, and preparation, of constitutively active Stat proteins capable of transcriptional activation in a cell line in the absence of tyrosine phosphorylation is a principal object of the present invention. Numerous utilities of such compositions are provided, some of which are described herein. For example, transient transfection of a reporter gene with Stat3 DNA binding sites into various cell types cells may be used to test transcriptional activation by Stat3 or Stat3-C, both with and without induction of tyrosine phosphorylation. To induce tyrosine phosphorylation, cells are either treated with IL-6 plus soluble IL-6 receptor or co-transfected with v-src, both of which phosphorylate Stat3 and Stat3-C. As will be shown in the Examples, without any induced tyrosine phosphorylation, Stat3-C activated transcription of the reporter gene in all three cell lines approximately 10-fold above background while the wild-type Stat3 did not induce transcription. Upon induction of tyrosine phosphorylation with either IL-6 or v-src, transcriptional stimulation by wild-type Stat3 now became evident and a further increase of Stat3-C dependent transcription also occurred. These means for evaluating the activity of the constitutively active Stat are used in screening assays to evaluate the effectiveness of agents in modulating the binding of Stat to target DNA, modulating the dimerization of Stat, preferably to identify agents capable of blocking cellular transformation by Stat and the development of dysproliferative cells.

Detection of the activities of constitutively active Stat and the effect of agents thereon may be determined in both a cell-free system and in cell-based systems. For evaluation in a cell-free system, extracts of cells expressing the constitutively active Stat protein may be combined with target DNA sequences in which activity can be monitored by methods such as but not limited to detecting binding of the Stat protein to the DNA, transcriptional activation as determined by reporter genes in constructs also comprising a Stat protein binding region. The effect of added agents on Stat activity may be monitored by comparing the activity readout in the presence and the absence of the agent. Other means for monitoring activation are described in the citations herein, and in particular, U.S. Pat. No. 5,716,622, issued Feb. 10, 1998, incorporated herein by reference.

In cellular systems, cells may be transiently or stably transfected with a constitutively active Stat protein, and any one of a number of methods may be used to detect Stat activity and the effect of agents thereon. For example, immortalized fibroblasts transfected with the an expression vector encoding Stat3 -C may be plated for growth in soft agar. Transformants were detected by their ability to form colonies in the agar. Another means of detection is the change in nuclear-cytoplasmic distribution of the Stat molecules in the parent cell and transformed cells. Wild-type Stat molecules are known to accumulate in the nucleus after phosphorylation. The use of an epitope tag, such as FLAG, in the construct used to transfect cells aids in the detection of the change in nuclear accumulation of the modified Stat protein.

Other means for detection include measurement of the binding to Stat DNA binding sites. The extent of binding in the presence and absence of a suspect modulating agent may be evaluated therein.

Another means for evaluating the effect of agents on the activity of the modified Stat protein of the present invention in cells is monitoring the effect of agents on the transformation of transfected cells. As will be shown in the Examples below, it was found that cells expressing Stat3-C are tumorigenic. For example, when $10^6$ cells from either of two Stat3-C clones were injected subcutaneously into nude mice, tumors became apparent at the site of injection within 2 to 4 weeks. Western blot analysis of extracts derived from Stat3-C containing tumors reveal high levels of Flag-tagged Stat3-C protein showing that the growing tumor cells retain this protein. These detection methods provide means for evaluating the effect of agents on modulation of transformation. Preferably, the methods disclosed herein are used to identify agents capable of reducing or blocking the tumorigenic ability of Stat proteins. Such agents have utility in the treatment of various dysproliferative disease, of which several have been found to have constitutively active Stat proteins (see Background). Such diseases include a variety of cancers and psoriasis. In another embodiment, the methods of identifying agents capable of modulating Stat protein activity may be used to identify agents capable of inducing cell growth and proliferation to promote the growth and immortalization of cells. Such agents may be useful in promoting the regeneration of tissues and organs; for example, repopulating the bone marrow, and the regrowth of skin and gut epithelium.

Other means for detecting the effect of agents on the transformation brought about by constitutively activated Stat3-C is based on transcription of genes regulated by Stat3 binding to regulatory regions. Detection methods based on identifying these genes is embraced in the present invention. By way of non-limiting example, an assay of the transcriptional activation of reporter genes bearing Stat3 dependent enhancer containing chromosomal segments may be prepared; in another embodiment, enhanced expression of genes that are known to be connected either to growth control or apoptotic events may be monitored. Using the rat $\alpha_2$-macroglobulin promoter (Hattori et al., 1990) and the human cyclin D1 promoter DNA segments (Lee et al., 1999) in reporter gene constructs introduced into 293T cells to test transcriptional activation by Stat3-C, it was shown that Stat3-C increased transcription 10-fold with the $\alpha$2-macroglobulin construct and 40-fold with the cyclin D1 construct without IL-6 treatment or v-src cotransfection. Additional increases were seen after IL-6 treatment and or v-src cotransfection. Transcriptional stimulatory ability of Stat3-C in the transformed cell lines was also evaluated. 3Y1, Stat3-C and v-src cell lines were transiently transfected with the cyclinD1 luciferase reporter gene. Both cell lines transformed by Stat3-C or by v-src gave constitutive transcriptional signals that were significantly greater than in 3Y1 cells. To test the effect of Stat3-C on endogenous genes the mRNA levels of cyclin D1, Bc1-$x_L$, and c-myc were determined in Northern blots from untransformed 3Y1 cells, and these same cells transformed by v-src or by Stat3-C. There was a distinct increase in the concentration of each of these mRNAs. These further examples illustrate the various detection means embraced within the present invention which take advantage of a constitutionally active Stat protein to monitor the role of Stat in gene activation, cellular transformation and tumorigenesis, and can be likewise used to screen compounds capable of modulating these activities.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE I

Materials and Methods

Cell Lines, Transfections, and Luciferase Measurements.

NIH3T3, 293T and HepG2 cells were obtained from the American Type Culture Collection. 3Y1 cells (Kimura et al., 1975). V-src and v-Eyk transformed NIH3T3 and 3Y1 cells were a generous gift from H. Hanafusa and D. Besser (Rockefeller University). All cells were grown in Dulbecco's modified Eagle's medium (DMEM) containing 10% Cosmic Calf serum (HyClone). Total cell extracts and nuclear and cytoplasmic factors were prepared as described with the exclusion of NP-40 in the cytoplasmic extract buffer (Shuai et al., 1992; Wen et al., 1995). Lipofectamine Plus (Life Technologies) or Superfect (Qiagen) was used for transfections. Typically, for a 35 mm-diameter dish containing $1\times10^5$ cells, 1 g of each plasmid to be transfected was utilized. For IL-6 induction experiments, 20 hrs after transfection of luciferase containing reporter genes, human IL-6 (Boehringer Mannheim) was used at a concentration of 500 U/ml and recombinant soluble form of the human IL-6 receptor (R&D Systems) was used at 5 ng/ml for approximately 6 hrs prior to preparing extracts. Luciferase assays were performed using the dual-luciferase reporter system (Promega) and all the results shown indicate luciferase activities normalized against an internal control luciferase reporter of Renilla luciferase (Promega).

Colony Growth in Soft Agar

Soft agar assays were performed as previously described (Bromberg et al., 1998). Essentially, growth in soft agar was determined in 35 mm diameter dishes prepared with a lower layer of 0.7% Agar (BiTek, DIFCO) solution in DMEM with 10% Cosmic Calf Serum (HyClone) containing either 800 mg/ml of G418 sulfate (Geneticin; Life Technolgies or 2 mg/ml of puromycin (Sigma); then overlaid with a 0.35% agar solution, also in growth medium, in which $1\times10^5$ transfected cells were resuspended. Colonies were scored 21 days after preparation (colonies larger than ~0.1 mm in diameter were scored as positive). Stat3- C transformed 3Y1 cells were maintained in DMEM with 10% Cosmic Calf Serum and 800 mg/ml of G418 sulfate.

Tumor Growth in Nude Mice

Four to six week old athymic, Balb-c/nu/nu mice were injected with $1\times10^6$ cells in 200 ml PBS from various cell lines (3Y1, v-src, Stat3-C, v-Eyk). After 3 weeks tumors were measured. Each cell line was tested in 3 different animals.

Plasmids Western Blots, EMSAs and Northern Blots

Murine Stat3 was cloned into RcCMV-Neo (InVitrogen) tagged at the 3' end with a FLAG epitope (Wen et al., 1995; Bromberg et al., 1998). The Stat3-C construct was made by site-directed mutagenesis (Quick-Change by Promega) using primer pairs 5' GCTATAAGATCATGGATTGTACC TGCATCCTGGTGTCTCC (SEQ ID NO:6). pBabe/v-src was a gift from H. Hanafusa. The cyclin D1 Luciferase—1745 promoter construct was a gift from R. Pestell (Lee et al., 1999). The luciferase reporter plasmid that was used contained four copies of the m67 high affinity binding site (Wagner et al., 1990) for Stat1 and Stat3 followed by the luciferase gene (Besser et al., 1999). The rat $\alpha_2$-macroglobulin luciferase promoter construct, pRat a2 MG HH 1.2 was a gift from Georg Fey (Scripps Clinic) (Hattori et al., 1990). The Renilla luciferase construct (Promega) was utilized in transfection experiments in order to normalize for transfection efficiency. Nuclear and cytoplasmic extracts were prepared as previously described (Wen et al., 1995). Cells were scraped off the dish and pelleted; 3× the pellet volume of cytoplasmic buffer was added (20 mM Hepes pH 7.9, 10 mM KCl, 0.1 mM NaVanadate, 1 mM EDTA, 10% Glycerol, 1 mM DTT, 1 mM PMSF) and left on ice for 10 mins. The sample was lysed using a dounce homogenizer (10–20 strokes) and spun in an Eppendorf centrifuge for 5 mins. The supernatant is the cytoplasmic fraction. The pellet was washed once with cytoplasmic buffer, then resuspended in 2× the pellet volume with nuclear buffer (420 mM NaCl, 20% Glycerol, 20 mM Hepes pH 7.9, 10 mM KCl, 1 mM EDTA, 0.1 mM NaVanadate, 1 mM PMSF, 1 mM DTT) Protein concentration was determined by the Bradford assay (BioRad). Western blots were carried out by standard methods (Ausubel et al., 1994). Anti-Stat3 serum, which was previously described (Zhong et al., 1994b; Zhong et al., 1994a) was diluted 1:1000 for Western blotting. Anti-phospho tyro sine Stat3 (Tyr705) antibody (New England Biolab) was used at a 1:5000 dilution and an anti-phospho serine Stat3 (Ser 727) antibody (New England Biolab) at a 1:1000 dilution for Western blotting. Anti-FLAG monoclonal antibody Kodak/IBI) was used at a 1:1000 dilution for Western blotting and at a 1:10 dilution for supershifting DNA-protein complexes. Electrophoretic mobility shift assays (EMSA) were performed as previously described (Vinkemeier et al., 1996). Nuclear extracts (2–3 mg protein) from cell lines or transfected cells were incubated with 1 ng of $^{32}$P-labeled m67 (5'-dGATTTCCCGTAAATCAT-3' [SEQ ID NO:7]) in a 10 ml reaction volume containing DNA binding buffer [20 mM Hepes pH 7.9, 4% Ficoll, 40 mM KCl, 10 mM $MgCl_2$, 10 mM $CaCl_2$, 1 mM DTT, 200 ng poly dIdC (Pharmacia Biotech)]. Dissociation rate determination was performed as previously described (Vinkemeier et al., 1996). RNA was isolated using Trizol Reagent (Gibco BRL). Northern blots were performed as previously described (Ausubel et al., 1994). The human Cyclin D1 probe was a gift from Richard Pestell.

EXAMPLE II

Design of a Constitutively Activated Stat3 Molecule

The crystal structures of Stat1 and Stat3 are virtually superimposable. The DNA bound dimers make protein:protein contact only in the —SH2 domains. The phosphotyrosine (residues 701 in Stat1 and 705 in Stat3) of one monomer is extended on a ~17 amino acid unstructured tether to bind to the R602 (Stat1) or R608 (Stat3) in the SH2 pocket of its partner; a reciprocal interaction completes the contacts between the two monomers. In both the Stat1 or Stat3 homodimer there are loops just N-terminal to the —COOH end of the SH2 domain that are in close proximity to one another (FIG. 1A). Substituting cysteine residues for A662 and N664 of the Stat3 molecule should allow for sulfhydral bonds to form between Stat3 monomers (FIGS. 1B and 1C) and render the molecule capable of dimerizing without a phosphate on Y705. Such a molecule, Stat3-C, was made by site-directed mutagenesis of wild-type Stat3. The codon at the position corresponding to A662, GCG, was changed to TGT; the N at 664, AAC, was changed to TGC. An epitope tag (FLAG) was also appended for ease in following the molecule in cells.

EXAMPLE III

Biochemical Analysis of Stat3-C

Figure 2B:
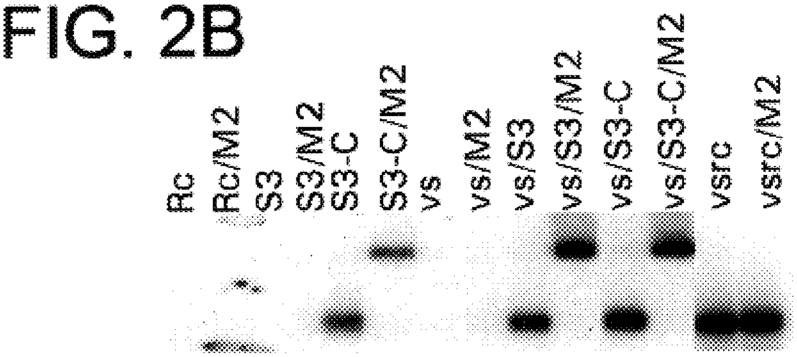

Both wild-type Stat3 and mutant Stat3-C Flag-tagged proteins were introduced by transient transfection into 293T cells. Western blot analysis of nuclear extracts from serum grown cells transfected with Stat3-C revealed production of a protein that was serine phosphorylated but not tyrosine phosphorylated (FIG. 2A). Stat3 taken from growing cells was phosphorylated on serine without serum starvation (Wen et al., 1995; Zhu et al., 1997).] When the cDNA encoding the tyrosine kinase v-src was co-transfected with either Stat3 or Stat3-C, both molecules became tyrosine phosphorylated (FIG. 2A). The monomers of Stat3-C migrated slightly faster than wild-type Stat3 in SDS/PAGE. Electrophoretic mobility shift analysis (EMSA) using nuclear extracts of these cells and assaying binding to a high-affinity binding site (M67) for Stat3 was carried out both with and without v-src cotransfection. Without the v-src there was no binding of wild-type Stat3 but there was constitutive binding of Stat3-C to DNA (FIG. 2B, lane 5). In the cells co-transfected with v-src, the now tyrosine phosphorylated wild-type Stat3 bound to DNA (FIG. 2B, lane 9). Also there was increased binding to DNA in extracts from cells transfected with Stat3-C plus v-src. Thus either more dimers of Stat3-C formed when tyrosine phosphorylation was stimulated or the affinity for DNA was greater (FIG. 2B, lane 11, see next section). The Flag-tagged Stat3-C protein-DNA complexes could be supershifted with anti-Flag-antibody, while tyrosine phosphorylated Stat3 protein which was not epitope tagged was not affected by this antiserum (FIG. 2B, lane 14).

EXAMPLE IV

Nature of Stat3-C Dimer

Figure 2C:
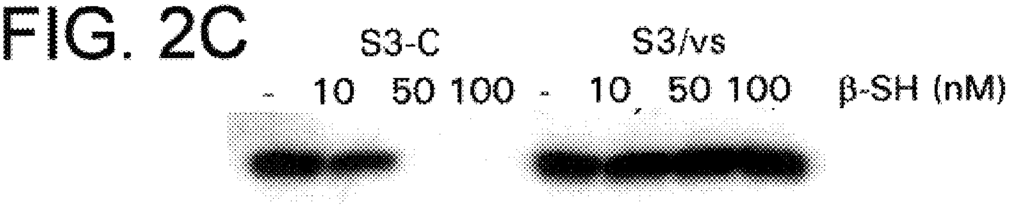

If the Stat3-C dimerized through sulfhydral bonds between monomers, the formation of dimeric DNA binding complexes should be inhibited by a reducing agent. Nuclear extracts containing either constitutively activated Stat3-C or tyrosine phosphorylated Stat3 (Stat3 from cells co-transfected with v-src) were incubated with increasing concentrations of β-mercaptoethanol. Stat3-C DNA binding as determined by EMSA was much more susceptible to inhibition by β-mercaptoethanol than wild-type protein (FIG. 2C), supporting the conclusion that a sulfhydral bond (s) between monomers was responsible for Stat3-C dimerization and DNA binding.

Figure 2D:
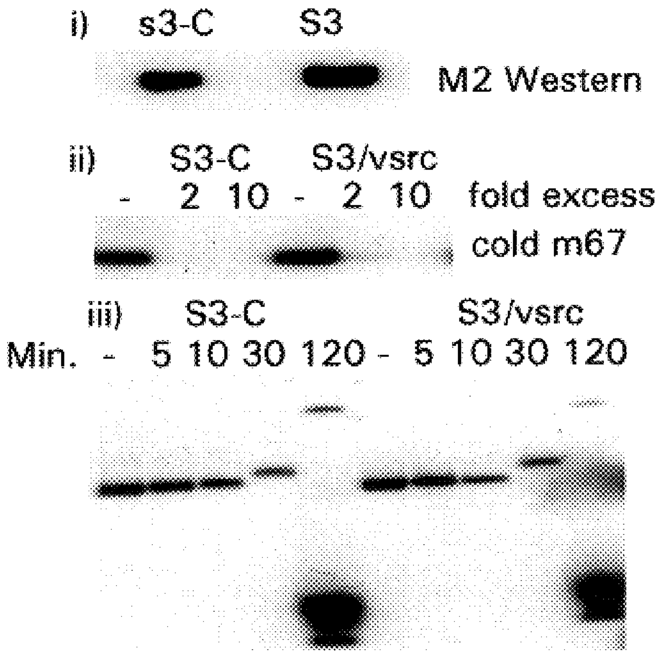

The relative affinity of both Stat3-C and tyrosine phosphorylated Stat3 for the high affinity m67 DNA binding site was compared. Simultaneous addition of labeled and unlabeled oligonucleotide with nuclear extract prevented Stat:DNA complex formation about equally (FIG. 2D, ii). The stability of preformed protein:DNA complexes was then evaluated. Formation of a complex was allowed to occur between a fixed amount of nuclear extract containing Stat3-C or phosphorylated Stat3 (FIG. 2D, i, M2 Western) with labeled oligonucleotide (M67); then a 100-fold excess of unlabeled oligonucleotide was added to the preformed complex. Aliquots were withdrawn at intervals and immediately examined by loading onto an electrophoresis gel. The dissociation of both Stat3-C and Stat3 from the oligonucleotide were very similar and the halftime for dissociation was estimated to be 17 minutes (FIG. 2D, iii).

EXAMPLE V

Stat3-C Activates Transcription Constitutively

Figure 3A:
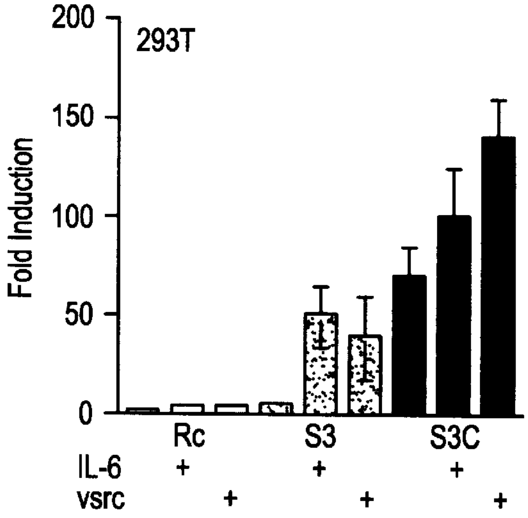
FIGS. 3A–3C show transcriptional activity of Stat3-C. (A) 293T cells were co-transfected with an m67 luciferase reporter construct and RcCMV (Rc), Stat3 (S3) or Stat3-C (S3C). Some samples (as indicated) were either co-transfected with v-src or treated with IL-6 and soluble IL-6 receptor for 6 hrs before assaying for luciferase activity. Results shown are the mean±standard deviation of 3–5 experiments performed in triplicate. (B) NIH3T3 or 3Y1 cells were transfected as described above and co-transfected with v-src. (C) HepG2 cells were also transfected as described above. HepG2 cells were not transfected with v-scr.
Figure 3B:
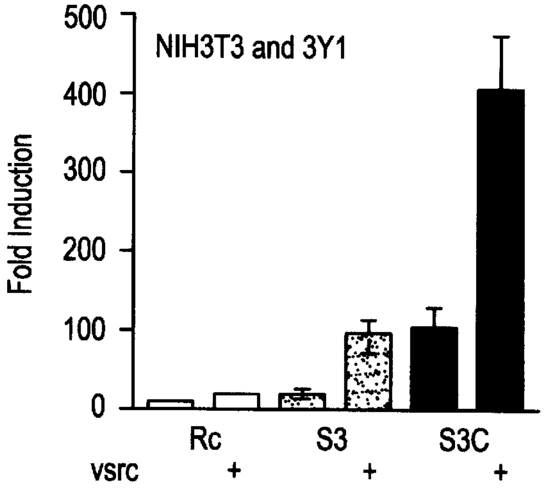
Figure 3C:
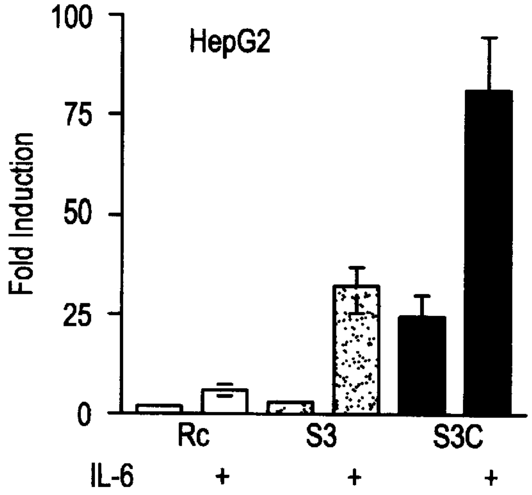

Transient transfection of a reporter gene with Stat3 DNA binding sites into 293T, 3Y1, NIH3T3, and HepG2 cells was used to test transcriptional activation by Stat3 or Stat3-C. Transcriptional activation was assayed both with and without induction of tyrosine phosphorylation. In order to induce tyrosine phosphorylation, cells were either treated with IL-6 plus soluble IL-6 receptor or co-transfected with v-src both of which phosphorylate Stat3 and Stat3-C. Without any induced tyrosine phosphorylation, Stat3-C activated transcription of the reporter gene in all three cell lines approximately 10-fold above background while the wild-type Stat3 did not induce transcription (FIG. 3). Upon induction of tyrosine phosphorylation with either IL-6 or v-src, transcriptional stimulation by wild-type Stat3 now became evident and a further increase of Stat3-C dependent transcription also occurred. This latter result accorded with the increase in DNA binding of Stat3-C after induction of tyrosine phosphorylation (FIG. 2B, lane 11).

EXAMPLE VI

Preparation and Characterization of a Constitutively Active Stat1 Molecule

Following the procedures described in the Examples above, a modified human Stat1 molecule was prepared using site-directed mutagenesis, with the A residue at position 656 changed to C (codon GCT to TGT), and the N residue at position 658 changed to C (codon AAT to TGT) (SEQ ID NO:8; polynucleotide sequence SEQ ID NO: 10). Characterization following the procedures as described above showed that the modified Stat1 molecule was capable of dimerizing spontaneously, binding to DNA, and activating transcription.

EXAMPLE VII

Characterization of Cell Lines Expressing Stat3-C

NIH3T3 and rat 3Y1 immortalized fibroblasts were transfected with the empty vector RcCMV, or the expression vector encoding Stat3, Stat3-C, or v-src and the transfected cells were plated for growth in soft agar. Both NIH3T3 cells and 3Y1 cells were transfected with RcCMV, Stat3, Stat3-C or v-src. Transfected cells ($1\times10^5$) were plated in soft agar. Three weeks later colony number was determined. Results shown are the mean +/− standard deviation (SD) of 3–8 experiments. The plating efficiency of representative cell lines (either derived from soft agar (SA) or from clones selected in G418) was determined by plating the indicated number of cells into soft agar and counting colonies after 4–10 days. Colonies 0.1 mm or greater were counted. No transformants were detected with either RcCMV or wild-type Stat3 (Table 1).

TABLE 1

Transformation Assay - Colonies in Soft Agar

| Vector | NIH3T3 - Transformation Assay: Colony Number (SD) | 3Y1 - Transformation Assay: Colony Number (SD) |
|---|---|---|
| Rc | 0 (0) | 0 (0) |
| Stat3 | 0 (0) | 0 (0) |
| Stat3-C | 12 (3) | 10 (4) |
| vsrc | 68 (10) | 137 (23) |

Plating Efficiency of Stable 3Y1Derived Cell Lines

| Cell Line | Cell Number | Colony Number |
|---|---|---|
| 3Y1/Rc | $10^6$ | 0 (0) |
| S3-C(SA) | $10^4$ | 90 (10) |
| S3-C(G418) | $10^4$ | 110 (20) |
| vsrc | $10^3$ | 100 (27) |

Figure 4A:
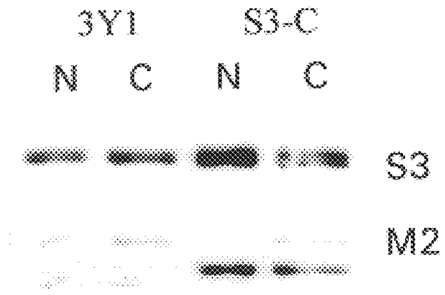
FIGS. 4A–4D depict stable transformed cell lines expressing Stat3-C. (A) Nuclear and cytoplasmic extracts (10 mg each), from 3Y1 and Stat3-C (S3-C) transformed cells were analyzed by western blot, probed with anti-Stat3 antibody (S3), stripped and reprobed with anti-Flag antibody (M2). (B) Nuclear extracts from 3Y1, v-src and Stat3-C (S3-C) were incubated with radiolabeled m67 and resolved on a non-denaturing polyacrylamide gel. Stat3-C (S3-C) containing extracts are supershifted with anti-Flag (M2) antibody. (C) 3Y1, Stat3-C or v-src transformed cell lines were transiently transfected with an m67 Luciferase reporter construct. Twenty hrs after transfection cells were harvested and assayed for luciferase activity (see Experimental Procedures). Results shown are the mean±standard deviation of 3 experiments performed in triplicate. (D) 3Y1, Stat3-C and v-scr transformed cell lines were plated in dishes as well as in soft agar for morphological comparisons and the measurement of cloning efficiency.

However, soft agar colonies were obtained with Stat3-C at a frequency about 1/10 of that caused by v-src (Table 1). Cells were recovered from these transformed colonies and cultured so that they could be further analyzed for the presence of Stat3-C protein, for constitutive transcriptional activity and for plating efficiency in soft agar in comparison to v-src transformed cells. In addition, 3Y1 cells were transfected with Stat3-C and G418 resistant clones were isolated. The G418 resistant clones plate in soft agar with similar efficiencies as with those originally isolated from soft agar. 3Y1 transformed cell lines rather than NIH3T3 cell lines were analyzed because of the occasional spontaneous transformation that is known to occur with NIH3T3 cells. When examined by Western blots, all of the independent cells lines established from soft agar colonies caused by Stat3-C (FLAG) expressed this protein (FIG. 4A).

The nucleo-cytoplasmic distribution of the Stat3 molecules in the parent cell and transformed cells, as shown in (FIG. 4A), was of interest. Wild-type Stat molecules are known to accumulate in the nucleus after phosphorylation although the basis for this accumulation; that is, whether speedier import or slower export is responsible for the shift in distribution, remains unknown. Western blots of nuclear and cytoplasmic extracts were compared using a Stat3 antiserum that detects the pre-existent wild-type Stat3 plus the newly incorporated Stat3-C or using the anti-Flag antiserum, M2, that only detects Stat3-C. Equal amounts of protein from the nucleus and cytoplasm were used in this experiment. In the untransformed 3Y1 cells the cytoplasmic signal was similar to the nuclear signal but since ~90% of the total cell protein is cytoplasmic this indicates most wild-type Stat3 is cytoplasmic without ligand stimulation. However extracts from the Stat3-C transformed cells showed a considerably stronger nuclear than cytoplasmic signal for Stat3. Also in the Stat3-C transformed cells the nuclear anti-Flag signal was greater than the cytoplasmic. These results make it clear that compared to wild-type protein the Stat3-C protein accumulates in the cell nucleus without ligand treatment of the cells. The two Stat3 bands seen in FIG. 4A are very likely the result of serine phosphorylation which is known to be responsible for two electrophoretically separable Stat3 molecules (Boulton et al., 1995; Wen et al., 1995).

Figure 4C:
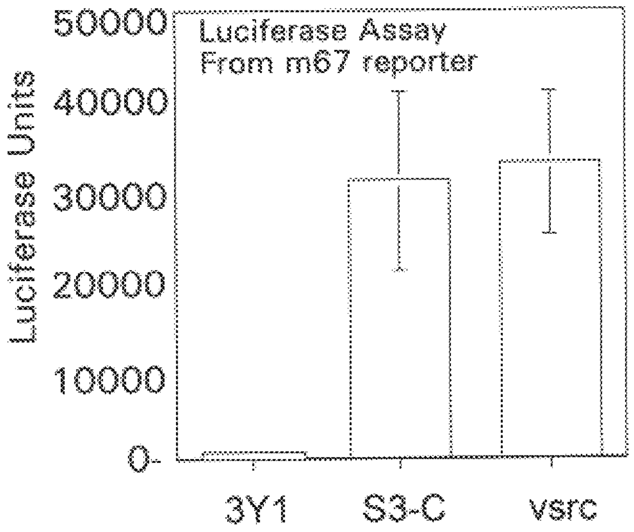
Figure 4B:
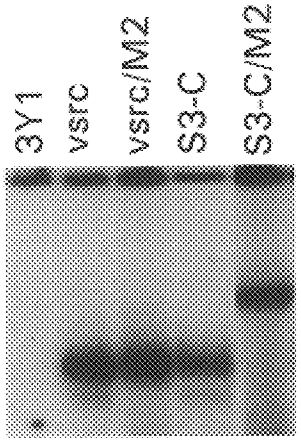

Extracts derived from stable cell lines expressing Stat3-C (Flag) exhibited constitutive binding to Stat3 DNA binding sites (FIG. 4B). Moreover, the amount of DNA binding activity in the Stat3-C cells was about one-half of that observed in a v-src transformed cell line where the endogenous Stat3 is activated (FIG. 4B, vsrc versus S3-C). Protein from these stable Stat3-C expressing cell lines has been precipitated by the Flag epitope and shown to contain no detectable phosphotyrosine (data not shown).

To examine the transcriptional stimulatory ability of Stat3-C in the transformed cell lines. 3Y1 -Stat3-C and v-src cell lines were transiently transfected with a luciferase reporter gene containing Stat3 DNA binding sites (M67×4; FIG. 4C). Both cell lines transformed by Stat3-C or by v-src gave constitutive transcriptional signals that were approximately equal and significantly greater than in 3Y1 cells.

Figure 4D:
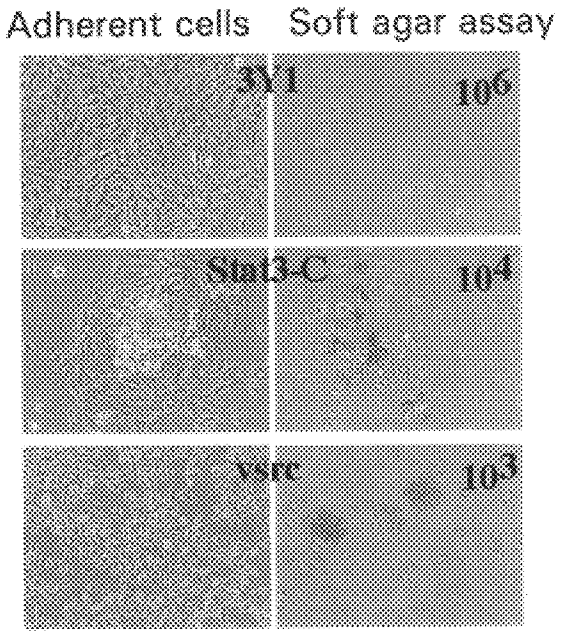

The plating efficiency in soft agar of the newly established Stat3-C transformed cell lines relative to that of v-src transformed cells were determined directly. Cells ($1\times10^6$) from 3Y1, v-src and two independent Stat3-C cell lines (21 and 1.4) were injected into the flank of 4–6 week old athymic nude (Balb-c nu/nu) mice. Each cell line was determined in 3 different animals. Tumor size was determined 3 weeks after injection. The number of colonies formed per cell plated (cloning efficiency) was about 1/100 for Stat3-C and 1/10 for v-src (Table 1, Table 2 and FIG. 4D). Morphologically, the soft agar colonies formed from Stat3-C cells were not as dense as those formed with v-src (FIG. 4D).

TABLE 2

Tumors in Nude Mice

| Cell Line | Tumor Size (cm) | $cm^3$ |
|---|---|---|
| 3Y1 | 0 | 0 |
| Stat3-C, Clone 21 | 0.4 × 0.5 × 1.0 | 0.2 |
| | 0.5 × 0.5 × 1.0 | 0.25 |
| | 0.3 × 0.9 × 1.0 | 0.3 |
| Stat3-C, Clone 1.4 | 2.0 × 1.0 × 0.5 | 1.0 |
| | 1.5 × 1.0 × 1.0 | 1.5 |
| | 1.0 × 2.0 × 0.5 | 1.0 |
| v-Src | 2.0 × 3.0 × 3.5 | 21 |
| | 4.0 × 2.0 × 2.0 | 16 |
| | 3.3 × 2.1 × 2.3 | 16 |

EXAMPLE VIII

Cells Expressing Stat3-C Are Tumorigenic

Figure 5A:
FIGS. 5A–5C show that cells expressing Stat3-C are tumorigenic. (A) A tumor in the flank of a nude mouse (in the foreground) injected with Stat3-C containing cells (cell line 21). None are seen when 3Y1 cells are injected. (B) Whole cell extracts (20 mg) from a v-src and Stat3-C derived tumor and the corresponding cell lines were analyzed by western blot. One blot was probed with anti-Stat3 antibody (S3) the other with anti-Flag antibody (M2). (C) Paraffin sections from v-src and Stat3-C containing tumors were stained with hematoxylin and eosin and viewed at 40× and 100× magnification.
Figure 5B:
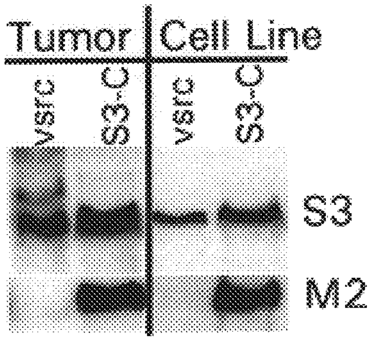
Figure 5C:
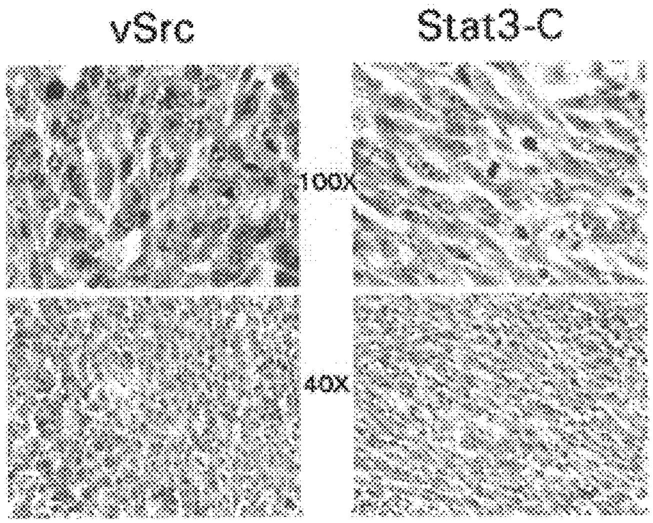

When $10^6$ cells from either of two Stat3-C clones were injected subcutaneously into nude mice, tumors became apparent at the site of injection within 2 to 4 weeks (Table 2 and FIG. 5A). No mice injected with parental 3Y1 cells developed tumors within an 8 week observation period. V-src transformed 3Y1 cells exhibited a stronger tumorigenic phenotype, developing larger tumors after 3 weeks (Table 2). Injection into nude mice with cells transformed by v-Eyk (a receptor tyrosine kinase that also leads to constitutively active Stat3 in transformed cells) (Besser et al., 1999) developed tumors similar in size to those seen with Stat3-C (data not shown). Western blot analysis of extracts derived from Stat3-C containing tumors reveal high levels of Flag-tagged Stat3-C protein (FIG. 5B) showing that the growing tumor cells retain this protein. Hematoxylin and eosin staining of formalin fixed sections of v-src or Stat3-C derived tumors displayed somewhat different morphologies. The cells from Stat3-C derived tumors had multiple nucleoli, large nuclei and frequent mitoses but were more spindle-like and appeared to be more organized than the cells from the faster growing v-src derived tumors (FIG. 5C). These differences are similar to the morphological changes observed with the same cell lines grown adherently on plates (FIG. 4D).

EXAMPLE IX

Transcriptional Events Controlled by Stat3-C That May Be Related to Transformation The transformation brought about by constitutively activated Stat3-C presumably rests on transcription of genes regulated by Stat3 binding to regulatory regions. Analysis has been carried out following two experimental lines: a) an assay of the transcriptional activation of reporter genes bearing Stat3 dependent enhancer containing chromosomal segments, and b) testing for enhanced expression of genes that are known to be connected either to growth control or apoptotic events.

Figure 6A:
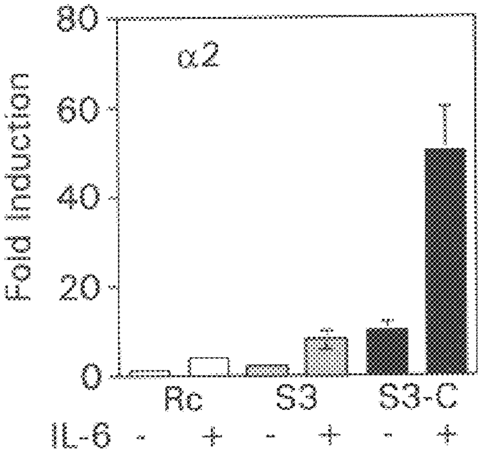
FIGS. 6A–6D depict Stat3-C gene targets. (A) 293T cells were co-transfected with a Rat $\alpha_2$-macroglobulin luciferase reporter construct and RcCMV (Rc), Stat3 (S3) or Stat3-C (S3-C). Some samples (as indicated) were treated with IL-6 and soluble IL-6 receptor for 6 hrs before assaying for luciferase activity. Results shown are the mean±standard deviation of 3 experiments performed in duplicate. (B) 293T cells were co-transfected with a human Cyclin D1 luciferase reporter construct and RcCMV (Rc), Stat3 (S3) or Stat3-C (S3-C). Some samples (as indicated) were either co-transfected with v-src or treated with IL-6 and soluble IL-6 receptor for 6 hrs before assaying for luciferase activity. Results shown are the mean±standard deviation of 3 experiments performed in duplicate. (C) 3Y1, Stat3-C or v-src transformed cell lines were transiently transfected with a Cyclin D1 Luciferase reporter construct. Twenty hrs after transfection cells were harvested and assayed for luciferase activity (see Experimental Procedures). Results shown are the mean±standard deviation of 3 experiments performed in duplicate. (D) RNA was isolated from 3Y1, v-src and Stat3-C (S3-C) transformed cell lines. Northern blot analysis was performed. The membrane was probed individually with cyclin D1, Bcl-$x_L$, c-myc and GAPHD as a control for loading.
Figure 6C:
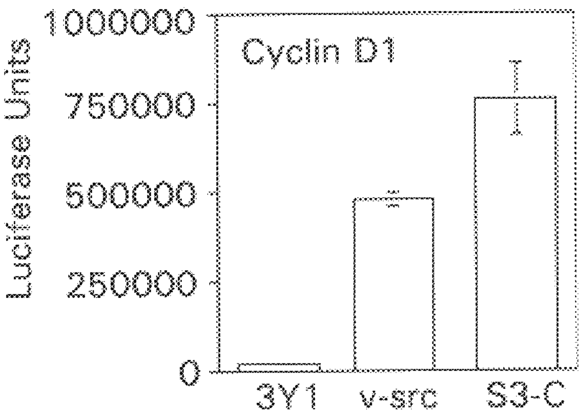
Figure 6B:
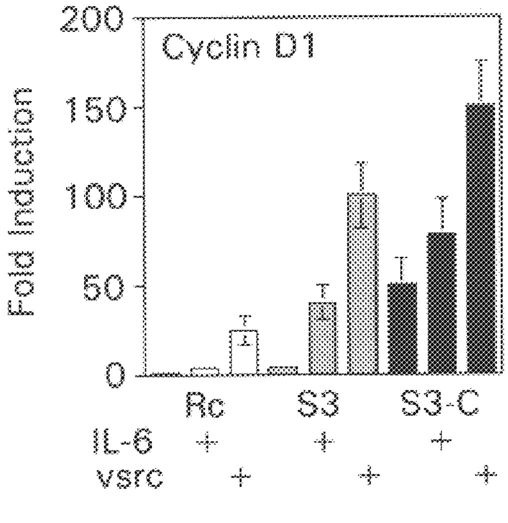

Transcription driven by the a2-macroglobulin enhancer is known to require both Stat3 and c-jun binding sites (Schaefer et al., 1995; Heinrich et al., 1998). Regions of these two proteins have been mapped that engage in physical contact, very likely during enhanceosome stimulation of transcriptional activation. In addition, it was recently reported that a 4-fold transcriptional stimulation of the cyclin D1 promoter was achieved through Stat5 binding (Matsumura et al., 1999). Both the rat a2-macroglobulin promoter (Hattori et al., 1990) and the human cyclinD1 promoter DNA segments (Lee et al, 1999) were used in reporter gene constructs introduced into 293T cells to test transcriptional activation by Stat3-C (FIGS. 6A and B.). Stat3-C increased transcription 10-fold with the a2-macroglobulin construct and 40-fold with the cyclin D1 construct without IL-6 treatment or v-src cotransfection. Additional increases were seen after IL-6 treatment and or v-src cotransfection. The transcriptional stimulatory ability of Stat3-C in the transformed cell lines was also examined. 3Y1, Stat3-C and v-src cell lines were transiently transfected with the cyclinD1 luciferase reporter gene. Both cell lines transformed by Stat3-C or by v-src gave constitutive transcriptional signals that were significantly greater than in 3Y1 cells (FIG. 6C).

Figure 6D:
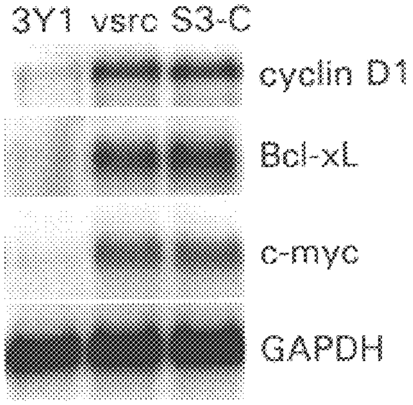

To test the effect of Stat3-C on endogenous genes the mRNA levels of cyclin D1, Bc1-$x_L$, and c-myc were determined in Northern blots from untransformed 3Y1 cells, and these same cells transformed by v-src or by Stat3-C. There was a distinct increase (~3- to 5-fold) in the concentration of each of these mRNAs (FIG. 6D).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

Alexander, W. S., Metcalf, D., and Dunn, A. R. (1995). Point mutations within a dimer interface homology domain of c-Mp1 induce constitutive receptor activity and tumorigenicity. Embo J 14, 5569–78.

Ausubel, F. M., Brent, R., Kingston, R. E., Moore, D. D., Seidman, J. G., Smith, J. A., and Struhl, K. (1994). Current Protocols in Molecular Biology. John Wiley & Sons, Inc.

Benitah, J. -P., Ranjan, R., Yamagishi, T., Janecki, M., Tomaselli, G. F., and Marban, F. (1997). Molecular motions within the pore of voltage-dependent sodium channels. Biophysical J. 73, 603–613.

Besser, D., Bromberg, J. F., Darnell, J. E., Jr., and Hanafusa, H. (1999). A single amino acid substitution in the v-Eyk intracellular domain results in activation of Stat3 and enhances cellular transformation. Mol Cell Biol 19, 1401–9.

Boulton, T. G., Zhong, Z., Wen, Z., Darnell, J. E., Jr., and Yancopoulos, G. D. (1995). Stat3 activation by cytokines utilizing gp130 and related transducers involves a secondary modification requiring an H7-sensitive kinase. Proc. Natl. Acad. Sci. USA 92, 6915–6919.

Bromberg, J. F., Horvath, C. M., Besser, D., Lathem, W. W., and Darnell, J. E., Jr. (1998). Stat3 activation is required for cellular transformation by v-src. Mol. Cell. Biol. 18, 2553–2558.

Bromberg, J. F., Horvath, C. M., Wen, Z., Schreiber, R. D., and Darnell, J. E., Jr. (1996). Transcriptionally active Stat1 is required for the antiproliferative effects of both IFN-a and IFN-g. Proc. Natl. Acad. Sci. USA 93, 7673–7678.

Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., Dalton, W. S., and Jove, R. (1999). Constitutive activation of Stat3 signaling confers resistance to apoptosis in human U266 myeloma cells. Immunity 10, 105–15.

Chen, X., Vinkemeier, U., Zhao, Y., Jeruzalmi, D., Darnell, J. E., Jr., and Kuriyan, J. (1998). Crystal structure of a tyrosine phosphorylated Stat-1 dimer bound to DNA. Cell 93, 827–839.

Cory, S., Vaux, D. L., Strasser, A., Harris, A. W., and Adams, J. M. (1999). Insights from Bcl-2 and Myc: malignancy involves abrogation of apoptosis as well as sustained proliferation. Cancer Res 59, 1685s–1692s.

Darnell, J. E., Jr. (1997). Stats and gene regulation. Science 277, 1630–1635.

Garcia, R., and Jove, R. (1998). Activation of Stat transcription factors in oncogenic tyrosine kinase signaling. J Biomed Sci 5, 79–85.

Grandis, J. R., Drenning, S. D., Chakraborty, A., Zhou, M. Y., Zeng, Q., Pitt, A. S., and Tweardy, D. J. (1998). Requirements of Stat3 but not Stat1 activation for epidermal growth factor receptor-mediated cell growth In vitro. J Clin Invest 102, 1385–92.

Haspel, R. L., Salditt-Georgieff, M., and Darnell, J. E., Jr. (1996). The rapid inactivation of nuclear tyrosine phosphorylated Stat1 depends on a protein tyrosine phosphatase. EMBO J. 15, 6262–6268.

Hattori, M., Abraham, L. J., Northemann, W., and Fey, G. H. (1990). Acute-phase reaction induces a specific complex between hepatic nuclear proteins and the interleukin 6 response element of the rat a2-macroglobulin gene. Proc. Natl. Acad. Sci. USA 87, 2364–2368.

Heinrich, P. C., Horn, F., Graeve, L., Dittrich, E., Kerr, I., Grotzinger, J., and A. Wollmer (1998). Interleukin-6 and related cytokines: effect on the acute phase reaction. Z Ernahrungswiss 37, 43–49.

Horvath, C. M., and Darnell, J. E., Jr. (1996). The antiviral state induced by alpha interferon and gamma interferon requires transcriptionally active Stat1 protein. J. Virol. 70, 647–650.

Kaplan, D. H., Shankaran, V., Dighe, A. S., Stockert, E., Aguet, M., Old, L. J., and Schreiber, R. D. (1998). Demonstration of an interferon gamma-dependent tumor surveillance system in immunocompetent mice. Proc Natl Acad Sci USA 95, 7556–61.

Kaplan, M. H., Schindler, U., Smiley, S. T., and Grusby, M. J. (1996). Stat6 is required for mediating responses to IL-4 and for the development of Th2 cells. Immunity 4, 313–319.

Kimura, G., Itagaki, A., and Summers, J. (1975). Rat cell line 3y1 and its vitrogenic polyoma- and sv40-transformed derivatives. Int J Cancer 15, 694–706.

Lee, R. J., Albanese, C., Stenger, R. J., Watanabe, G., Inghirami, G., Haines, G. K., 3rd, Webster, M., Muller, W. J., Brugge, J. S., Davis, R. J., and Pestell, R. G. (1999). pp60(v-src)induction of cyclin D1 requires collaborative interactions between the extracellular signal-regulated kinase, p38, and jun kinase pathways. A role for c-amp response element-binding protein and activating transcription factor-2 in pp60(v-src) signaling in breast cancer cells [In Process Citation]. J Biol Chem 274, 7341–50.

Liu, X., Robinson, G. W., Wagner, K. -U., Garrett, L., Wynshaw-Boris, A., and Hennighausen, L. (1997). Stat5a is mandatory for adult mammary gland development and lactogenesis. Genes & Devel. 11, 179–186.

Lodish, H., Baltimore, D., Berk, A., Zipursky, S. L., Matsudaira, P., and Darnell, J. (1995). Molecular Cell Biology, 3e. p. 1247–1294, Sci. Amer. Books, New York.

Matsumura, I., Kitamura, T., Wakao, H., Tanaka, H., Hashimoto, K., Albanese, C., Downward, J., Pestell, R. G., and Kanakura, Y. (1999). Transcriptional regulation of the cyclin D1 promoter by Stat5: its involvement in cytokine-dependent growth of hematopoietic cells. EMBO J. 18, 1367–1377.

Novak, U., Ji, H., Kanagasundaram, V., Simpson, R., and Paradiso, L. (1998). Stat3 forms stable homodimers in the presence of divalent cations prior to activation. Biochem. Biophys. Res. Commun. 247, 558–63.

Onishi, M., Nosaka, T., Misawa, K., Mui, A. L., Gorman, D., McMahon, M., Miyajima, A., and Kitamura, T. (1998). Identification and characterization of a constitutively active Stat5 mutant that promotes cell proliferation. Mol Cell Biol 18, 3871–9.

Schaefer, T. S., Sanders, L. K., and Nathans, D. (1995). Cooperative transcriptional activity of Jun and Stat3b, a short form of Stat3. Proc. Natl. Acad. Sci. USA 92, 9097–9101.

Schulteis, C. T., Nagaya, N., and Papazian, D. M. (1996). Intersubunit interaction between amino- and carboxyl-terminal cysteine residues in tetrameric shaker K+ channels. Biochem. 35, 12133–12140.

Shuai, K., Schindler, C., Prezioso, V. R., and Darnell, J. E., Jr. (1992). Activation of transcription by IFN-g: tyrosine phosphorylation of a 91 kD DNA binding protein. Science 259, 1808–1812.

Stark, G. R., Kerrr, I. M., Williams, B. R., Silverman, R. H., and Schreiber, R. D. (1998). How cells respond to interferons. Annu. Rev. Biochem. 67, 227–264.

Takeda, K., Clausen, B. E., Kaisho, T., Tsujimura, T., Terada, N., Forster, I., and Akira, S. (1999). Enhanced Th1 activity and development of chronic enterocolitis in mice devoid of Stat3 in macrophages and neutrophils. Immunity 10, 39–49.

Takeda, K., Kaisho, T., Yoshida, N., Takeda, J., Kishimoto, T., and Akira, S. (1998). Stat3 activation is responsible for IL-6-dependent T cell proliferation through preventing apoptosis: generation and characterization of T-cell-specific Stat3-deficient mice. J Immunol 161, 4652–60.

Takeda, K., Tanaka, T., Shi, W., Matsumoto, M., Minami, M., Kashiwamura, S., Nakanishi, K., Yoshida, N., Kishimoto, T., and Akira, S. (1996). Essential role of Stat6 in IL-4 signalling. Nature 380, 627–30.

Teglund, S., McKay, C., Schuetz, E., van Deursen, J. M., Stravopodis, D., Wang, D., Brown, M., Bodner, S., Grosveld, G., and Ihle, J. N. (1998). Stat5a and Stat5b proteins have essential and nonessential, or redundant, roles in cytokine responses. Cell 93, 841–50.

Tell, G., Scaloni, A., Pellizzari, L., Formisano, S., Pucillo, C., and Damante, G. (1998). Redox potential controls the structure and DNA binding activity of the paired domain. J Biol Chem 273, 25062–72.

Thierfelder, W. E., van Deursen, J. M., Yamamoto, K., Tripp, R. A., Sarawar, S. R., Carson, R. T., Sangster, M. Y., Vignali, D. A., Doherty, P. C., Grosveld, G. C., and Ihle, J. N. (1996). Requirement for Stat4 in interleukin-12-mediated responses of natural killer and T cells. Nature 382, 171–4.

Turkson, J., Bowman, T., Garcia, R., Caldenhoven, E., DeGroot, R. P., and Jove, R. (1998). Stat3 activation by Src induces specific gene regulation and is required for cell transformation. Mol Cell Biol 18, 2545–52.

Udy, G. B., Towers, R. P., Snell, R. G., Wilkins, R. J., Park, S. -H., Ram, P. A., Waxman, D. J., and Davey, H. W. (1997). Requirement of Stat5b for sexual dimorphism of body growth rates and liver gene expression. Proc. Natl. Acad. Sci. USA 94, 7239–7244.

Vinkemeier, U., Cohen, S. L., Moarefi, I., Chait, B. T., Kuriyan, J., and Darnell, J. E., Jr. (1996). DNA binding of in vitro activated Stat1a, Stat1b, and truncated Stat1: Interaction between NH2 terminal domains stabilizes binding of two dimers to tandem DNA sites. EMBO J. 15, 5616–5626.

Wagner, B. J., Hayes, T. E., Hoban, C. J., and Cochran, B. H. (1990). The SIF binding element confers sis/PDGF inducibility onto the c-fos promoter. EMBO J. 9, 4477–4484.

Watowich, S. S., Hilton, D. J., and Lodish, H. F. (1994). Activation and inhibition of erythropoietin receptor function: role of receptor dimerization. Mol Cell Biol 14, 3535–49.

Weber-Nordt, R. M., Mertelsmann, R., and Finke, J. (1998). The JAK-Stat pathway: signal transduction involved in proliferation, differentiation and transformation. Leuk Lymphoma 28, 459–67.

Wen, Z., Zhong, Z., and Darnell, J. E., Jr. (1995). Maximal activation of transcription of Stat1 and Stat3 requires both tyrosine and serine phosphorylation. Cell 82, 241–250.

Yu, C. L., Meyer, D., Campbell, G. S., Larner, A. C., Carter-Su, C., Schwartz, J., and Jove, R. (1995). Enhanced DNA-binding of a Stat3-related protein in cells transformed by the Src oncoprotein. Science 269, 81–83.

Zhong, Z., Wen, Z., and Darnell, J. E., Jr. (1994a). Stat3 and Stat4: Members of the family of signal transducers and activators of transcription. Proc. Natl. Acad. Sci. USA 91, 4806–4810.

Zhong, Z., Wen, Z., and Darnell, J. E., Jr. (1994b). Stat3: A Stat family member activated by tyrosine phosphorylation in response to epidermal growth factor and interleukin-6. Science 264, 95 . 98.

Zhu, X., Wen, Z., Xu, L. Z., and Darnell, J. E., Jr. (1997). Stat1 serine phosphorylation occurs independently of tyrosine phosphorylation and requires an activated Jak2 kinase. Mol. Cell. Biol. 17, 6618–6623.

Zong, C., Yan, R., August, A., Darnell, J. E., Jr., and Hanafusa, H. (1996). Unique signal transduction of Eyk: constitutive stimulation of the JAK-Stat pathway by an oncogenic receptor-type tyrosine kinase. Embo J 15, 4515–25.

What is claimed is:

1. A method for preparing Stat protein capable of constitutively dimerizing and binding to DNA in the absence of phosphorylation, comprising introducing in an unmodified Stat protein at least one cysteine residue, wherein said at least one cysteine residue of a first said modified Stat protein molecule is capable of interacting with said at least one cysteine residue of a second said modified Stat protein, forming a dimer.

2. The method of claim 1 wherein said unmodified Stat protein is selected from the group consisting of Stat1 (SEQ ID NO:1), Stat2 (SEQ ID NO:2), Stat3 (SEQ ID NO:3), and Stat4 (SEQ ID NO:4).

3. The method of claim 1 wherein said at least one cysteine residue is introduced into a conserved domain of said Stat protein.

4. The method of claim 3 wherein said domain is a C-terminal loop of the SH2 domain.

5. The method of claim 1 wherein said at least one cysteine residue is introduced by site-directed mutagenesis.

6. The method of claim 1 wherein a second cysteine residue is introduced into said Stat protein.

7. The method of claim 1 wherein said at least one cysteine residue and said Stat protein are selected from the group consisting of A656C or N658C or Stat1; L706C or I707C of Stat1; E653C or N655C of Stat2; L725C or G726C of Stat 2; F710C or I711C of Stat 3; A662C or N664C of Stat3; A651C or N653C of Stat4; F699C or I700C of Stat 4; G715C or S716C of Stat5; and S697C or H698C of Stat6.

8. The method of claim 6 wherein said at least one cysteine residue and second cysteine residue and said Stat proteins are selected from the group consisting of A656C and N658C of Stat1; L706C and I707C of Stat1; E653C and N655C of Stat2; L725C and G726C of Stat 2; F710C and I711C of Stat 3; A662C and N664C of Stat3; A651C and N653C of Stat4; F699C and I700C of Stat 4; G715C and S716C of Stat5; and S697C and H698C of Stat6.

9. The method of claim 1 wherein said Stat protein is Stat3.

10. The method of claim 9 wherein A 662 is changed to C 662 and N 664 is changed to C 664 (SEQ ID NO:5).

11. The method of claim 1 wherein said modified Stat protein further comprises an epitope tag.

12. The method of claim 11 wherein said epitope tag is FLAG.

13. A modified Stat protein capable of constitutively dimerizing and binding to DNA in the absence of phosphorylation, comprising at least one cysteine residue introduced into an unmodified Stat protein wherein said at least one cysteine residue on a first said modified Stat protein molecule is capable of interacting with said at least one cysteine residue of a second said modified Stat protein, forming a dimer.

14. The modified Stat protein of claim 13 wherein said unmodified Stat protein is selected from the group consisting of Stat1 (SEQ ID NO:1), Stat2 (SEQ ID NO:2), Stat3 (SEQ ID NO:3), and Stat4 (SEQ ID NO:4).

15. The modified Stat protein of claim 13 wherein said at least one cysteine residue is introduced into a conserved domain of said Stat protein.

16. The modified Stat protein of claim 15 wherein said conserved domain is a C-terminal loop of the SH2 domain.

17. The modified Stat protein of claim 13 wherein said at least one cysteine residue is introduced by site-directed mutagenesis.

18. The modified Stat protein of claim 13 wherein a second cysteine residue is present in Stat protein.

19. The modified Stat protein of claim 13 wherein said at least one cysteine residue and said Stat protein is selected from the group consisting of A656C or N658C of Stat1; L706C and I707C of Stat1; E653C and N655C of Stat2; L725C and G726C of Stat 2; F710C and I711C of Stat 3; A662C or N664C of Stat3; A651C and N653C of Stat4; F699C or I700C of Stat 4; G715C or S716C of Stat5; and S697C or H698C of Stat6.

20. The modified Stat protein of claim 18 wherein said at least one cysteine residue and said second cysteine residues and said Stat proteins are selected from the group consisting of A656C and N658C of Stat1; L706C and I707C of Stat1; E653C and N655C of Stat2; L725C and G726C of Stat 2; F710C and I711C of Stat 3; A662C and N664C of Stat3; A651C and N653C of Stat4; F699C and I700C of Stat 4; G715C or S716C of Stat5; and S697C and H698C of Stat6.

21. The modified Stat protein of claim 13 wherein said Stat protein is Stat3.

22. The modified Stat protein of claim 21 wherein A 662 is C 662 and N 664 is C 664 (SEQ ID NO:5).

23. The modified Stat protein of claim 18 further comprising a third cysteine residue or a third and a fourth cysteine residue.

24. The modified Stat protein of claim 13 wherein said modified Stat protein further comprises an epitope tag.

25. The modified Stat protein of claim 24 wherein said epitope tag is FLAG.

26. A method for identifying an agent capable of modulating dimerization of a Stat protein in the absence of tyrosine phosphorylation comprising:

a) providing a constitutively active Stat protein producing cell line;

b) introducing to a sample of cells from said cell line an agent suspected of modulating said dimerization; and c) examining said cells for a consequence of Stat protein dimerization by said agent.

27. The method of claim 26 wherein said consequence of Stat protein dimerization is selected from the group consisting of the extent of DNA binding in said cells by said Stat protein, oncogenesis in said cells as determined by morphological changes; colony formation by said cells, expression in said cells of a reporter gene in the cyclin D1 promoter; increased nuclear presence of Stat protein, development of an antiviral state, growth restraint secondary to IFN-$\gamma$ or IFN-$\alpha$ treatment, and apoptosis of said cells.

28. A method for identifying an agent capable of modulating dimerization of a Stat protein in the presence of tyrosine phosphorylation comprising:

a) providing a constitutively active Stat protein producing cell line;

b) introducing to a sample of cells from said cell line an agent suspected of modulating said dimerization;

c) providing a means for inducing tyrosine phosphorylation in said cell line; and d) examining said cells for a consequence of Stat protein dimerization by said agent.

29. The method of claim 28 wherein said means for inducing tyrosine phosphorylation is selected from the group consisting of transfecting said cells with v-src and treating said cells with a combination of IL-6 and soluble IL-6 receptor.

30. A method for identifying cells transformed by a constitutively active Stat protein comprising measuring the level of cyclin D1 mRNA in said cells, comparing said level to cyclin D1 mRNA levels in normal cells, and identifying cells transformed by said constitutively active Stat protein as those with a cyclin D1 message RNA level greater than normal.

31. A method for identifying an agent capable of modulating transcriptional activation of a reporter gene with a Stat DNA binding site comprising the steps of 1) transfecting a reporter gene with a Stat DNA binding site into a cell line;

2) transfecting said cell line to express a constitutively active Stat protein; and 3) correlating a change in the extent of expression of said reporter gene as a consequence of the presence of said agent with activity of said agent.

32. The method of claim 31 wherein said reporter gene is a m67-luciferase reporter gene construct or a cyclin D1-luciferase reporter gene construct.

33. The method of claim 31 additionally comprising means for inducing tyrosine phosphorylation in said cell line.

34. The method of claim 33 wherein said means for inducing tyrosine phosphorylation is selected from the group consisting of transfecting said cells with v-src and treating said cells with a combination of IL-6 and soluble IL-6 receptor.

35. A method for identifying an agent capable of modulating the interactions between a constitutively active Stat protein dimer and its target DNA sequence comprising:

a) providing a constitutively dimerizable Stat protein of claim 13;

b) providing a target DNA sequence;

c) introducing an agent to a mixture of (a) and (b);

d) determining the extent of association between said Stat protein and said target DNA; and e) correlating said association with the ability of said agent to modulate said interaction.

36. The method of claim 35 wherein step (a) is prepared from a nuclear extract of a cell transfected with a modified Stat protein.

37. The method of claim 35 wherein said agent interferes with said interaction.

38. The method of claim 35 wherein said agent promotes said interaction.

39. A method for identification of an agent capable of modulating cell growth or proliferation mediated by the interaction between a Stat protein and DNA in the absence of tyrosine phosphorylation comprising the steps of:

a) providing a constitutively active Stat protein producing cell line;

b) introducing to a sample of cells from said cell line an agent suspected of modulating said interaction; and c) examining said cells for a consequence of Stat protein interaction by said agent.

40. The method of claim 39 wherein said consequence of Stat protein interaction with DNA is selected from the group consisting of the extent of DNA binding in said cells by said Stat protein, oncogenesis in said cells as determined by morphological changes, colony formation by said cells, expression in said cells of a reporter gene in the cyclin D1 promoter, increased nuclear presence of Stat protein, development of an antiviral state, growth restraint secondary to IFN-$\gamma$ or IFN-$\alpha$ treatment, and apoptosis of said cells.

41. A method for identifying an agent capable of modulating dimerization of a Stat protein in the presence of tyrosine phosphorylation comprising the steps of:

a) providing a constitutively active Stat protein producing cell line;

b) introducing to a sample of cells from said cell line an agent suspected of modulating said interaction;

c) providing a means for inducing tyrosine phosphorylation in said cell line; and d) examining said cells for a consequence of Stat protein interaction by said agent.

42. The method of claim 41 wherein said means for inducing tyrosine phosphorylation is selected from the group consisting of transfecting said cells with v-src and treating said cells with a combination of IL-6 and soluble IL-6 receptor.

43. The method of claim 39 wherein said agent blocks transformation of said cell line.

44. A cell line expressing a modified Stat protein of claim 13.

45. The cell line of claim 44 wherein said cell line is capable of forming tumors in nude mice.

46. A method for identifying an agent capable of modulating the tumorigenesis by cells expressing a constitutively active Stat protein comprising the steps of (A) implanting said cells in nude mice;

(B) treating a mouse of step (a) with said agent;

(C) comparing the growth of a tumor from said cells in mice treated with said agent to mice not treated with said agent, thereby identifying an agent capable of modulating said tumorigenesis.

47. The method of claim 46 wherein said cells express a Stat protein of claim 13.

48. A method for identifying an agent capable of inhibiting cellular transformation comprising exposing a transformed cell line expressing a modified Stat protein of claim 13 to an agent suspected of inhibiting cellular transformation, followed by determining the effect of said agent on said cellular transformation.

49. The method of claim 48 wherein said determining said effect of said agent on said cellular transformation is selected from the group consisting of oncogenesis in said cells as determined by morphological changes; colony formation by said cells, expression in said cells of a reporter gene in the cyclin D1 promoter; increased nuclear presence of Stat protein, development of an antiviral state, growth restraint secondary to IFN-$\gamma$ or IFN-$\alpha$ treatment, and apoptosis of said cells.

50. A polynucleotide encoding the modified Stat protein of claim 13.

51. The polynucleotide sequence of claim 50 which is SEQ ID NO:9.

* * * * *

SEQUENCE LISTING

```
<160> NUMBER OF SEQ ID NOS: 10

<210> SEQ ID NO 1
<211> LENGTH: 750
<212> TYPE: PRT
<213> ORGANISM: Homo sapiens

<400> SEQUENCE: 1

Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Ala Ala Asn
         35                  40                  45

Asp Val Ser Phe Ala Thr Ile Arg Phe His Asp Leu Leu Ser Gln Leu
     50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
```

-continued

```
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
    530                 535                 540
```

-continued

Glu Asn Ile Asn Asp Lys Asn Phe Pro Phe Trp Leu Trp Ile Glu Ser
545 550 555 560

Ile Leu Glu Leu Ile Lys Lys His Leu Leu Pro Leu Trp Asn Asp Gly
565 570 575

Cys Ile Met Gly Phe Ile Ser Lys Glu Arg Glu Arg Ala Leu Leu Lys
580 585 590

Asp Gln Gln Pro Gly Thr Phe Leu Leu Arg Phe Ser Glu Ser Ser Arg
595 600 605

Glu Gly Ala Ile Thr Phe Thr Trp Val Glu Arg Ser Gln Asn Gly Gly
610 615 620

Glu Pro Asp Phe His Ala Val Glu Pro Tyr Thr Lys Lys Glu Leu Ser
625 630 635 640

Ala Val Thr Phe Pro Asp Ile Ile Arg Asn Tyr Lys Val Met Ala Ala
645 650 655

Glu Asn Ile Pro Glu Asn Pro Leu Lys Tyr Leu Tyr Pro Asn Ile Asp
660 665 670

Lys Asp His Ala Phe Gly Lys Tyr Tyr Ser Arg Pro Lys Glu Ala Pro
675 680 685

Glu Pro Met Glu Leu Asp Gly Pro Lys Gly Thr Gly Tyr Ile Lys Thr
690 695 700

Glu Leu Ile Ser Val Ser Glu Val His Pro Ser Arg Leu Gln Thr Thr
705 710 715 720

Asp Asn Leu Leu Pro Met Ser Pro Glu Glu Phe Asp Glu Val Ser Arg
725 730 735

Ile Val Gly Ser Val Glu Phe Asp Ser Met Met Asn Thr Val
740 745 750

<210> SEQ ID NO 2
<211> LENGTH: 851
<212> TYPE: PRT
<213> ORGANISM: Homo sapiens

<400> SEQUENCE: 2

Met Ala Gln Trp Glu Met Leu Gln Asn Leu Asp Ser Pro Phe Gln Asp
1 5 10 15

Gln Leu His Gln Leu Tyr Ser His Ser Leu Leu Pro Val Asp Ile Arg
20 25 30

Gln Tyr Leu Ala Val Trp Ile Glu Asp Gln Asn Trp Gln Glu Ala Ala
35 40 45

Leu Gly Ser Asp Asp Ser Lys Ala Thr Met Leu Phe Phe His Phe Leu
50 55 60

Asp Gln Leu Asn Tyr Glu Cys Gly Arg Cys Ser Gln Asp Pro Glu Ser
65 70 75 80

Leu Leu Leu Gln His Asn Leu Arg Lys Phe Cys Arg Asp Ile Gln Pro
85 90 95

Phe Ser Gln Asp Pro Thr Gln Leu Ala Glu Met Ile Phe Asn Leu Leu
100 105 110

Leu Glu Glu Lys Arg Ile Leu Ile Gln Ala Gln Arg Ala Gln Leu Glu
115 120 125

Gln Gly Glu Pro Val Leu Glu Thr Pro Val Glu Ser Gln Gln His Glu
130 135 140

Ile Glu Ser Arg Ile Leu Asp Leu Arg Ala Met Met Glu Lys Leu Val
145 150 155 160

Lys Ser Ile Ser Gln Leu Lys Asp Gln Gln Asp Val Phe Cys Phe Arg

-continued

```
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285

Gln Asp Asp Pro Leu Thr Lys Gly Val Asp Leu Arg Asn Ala Gln Val
    290                 295                 300

Thr Glu Leu Leu Gln Arg Leu Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
            340                 345                 350

Gly Asn Glu Ser Leu Thr Val Glu Val Ser Ile Asp Arg Asn Pro Pro
        355                 360                 365

Gln Leu Gln Gly Phe Arg Lys Phe Asn Ile Leu Thr Ser Asn Gln Lys
    370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Gly Ser Gly Lys Gly
                405                 410                 415

Ser Asn Lys Gly Pro Leu Gly Val Thr Glu Glu Leu His Ile Ile Ser
            420                 425                 430

Phe Thr Val Lys Tyr Thr Tyr Gln Gly Leu Lys Gln Glu Leu Lys Thr
        435                 440                 445

Asp Thr Leu Pro Val Val Ile Ile Ser Asn Met Asn Gln Leu Ser Ile
    450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
            500                 505                 510

Asn Ser Asp Gln Leu Ser Met Leu Arg Asn Lys Leu Phe Gly Gln Asn
        515                 520                 525

Cys Arg Thr Glu Asp Pro Leu Leu Ser Trp Ala Asp Phe Thr Lys Arg
    530                 535                 540

Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Arg Leu Leu Lys Lys
            580                 585                 590
```

-continued

Thr Met Ser Gly Thr Phe Leu Leu Arg Phe Ser Glu Ser Ser Glu Gly
595 600 605

Gly Ile Thr Cys Ser Trp Val Glu His Gln Asp Asp Asp Lys Val Leu
610 615 620

Ile Tyr Ser Val Gln Pro Tyr Thr Lys Glu Val Leu Gln Ser Leu Pro
625 630 635 640

Leu Thr Glu Ile Ile Arg His Tyr Gln Leu Leu Thr Glu Glu Asn Ile
645 650 655

Pro Glu Asn Pro Leu Arg Phe Leu Tyr Pro Arg Ile Pro Arg Asp Glu
660 665 670

Ala Phe Gly Cys Tyr Tyr Gln Glu Lys Val Asn Leu Gln Glu Arg Arg
675 680 685

Lys Tyr Leu Lys His Arg Leu Ile Val Val Ser Asn Arg Gln Val Asp
690 695 700

Glu Leu Gln Gln Pro Leu Glu Leu Lys Pro Glu Pro Glu Leu Glu Ser
705 710 715 720

Leu Glu Leu Glu Leu Gly Leu Val Pro Glu Pro Glu Leu Ser Leu Asp
725 730 735

Leu Glu Pro Leu Leu Lys Ala Gly Leu Asp Leu Gly Pro Glu Leu Glu
740 745 750

Ser Val Leu Glu Ser Thr Leu Glu Pro Val Ile Glu Pro Thr Leu Cys
755 760 765

Met Val Ser Gln Thr Val Pro Glu Pro Asp Gln Gly Pro Val Ser Gln
770 775 780

Pro Val Pro Glu Pro Asp Leu Pro Cys Asp Leu Arg His Leu Asn Thr
785 790 795 800

Glu Pro Met Glu Ile Phe Arg Asn Cys Val Lys Ile Glu Glu Ile Met
805 810 815

Pro Asn Gly Asp Pro Leu Leu Ala Gly Gln Asn Thr Val Asp Glu Val
820 825 830

Tyr Val Ser Arg Pro Ser His Phe Tyr Thr Asp Gly Pro Leu Met Pro
835 840 845

Ser Asp Phe
850

<210> SEQ ID NO 3
<211> LENGTH: 770
<212> TYPE: PRT
<213> ORGANISM: Mus musculus

<400> SEQUENCE: 3

Met Ala Gln Trp Asn Gln Leu Gln Gln Leu Asp Thr Arg Tyr Leu Lys
1 5 10 15

Gln Leu His Gln Leu Tyr Ser Asp Thr Phe Pro Met Glu Leu Arg Gln
20 25 30

Phe Leu Ala Pro Trp Ile Glu Ser Gln Asp Trp Ala Tyr Ala Ala Ser
35 40 45

Lys Glu Ser His Ala Thr Leu Val Phe His Asn Leu Leu Gly Glu Ile
50 55 60

Asp Gln Gln Tyr Ser Arg Phe Leu Gln Glu Ser Asn Val Leu Tyr Gln
65 70 75 80

His Asn Leu Arg Arg Ile Lys Gln Phe Leu Gln Ser Arg Tyr Leu Glu
85 90 95

Lys Pro Met Glu Ile Ala Arg Ile Val Ala Arg Cys Leu Trp Glu Glu

-continued

```
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Pro Glu Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525
```

-continued

```
Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Asp Leu Thr Ser Glu Cys Ala Thr Ser
        755                 760                 765

Pro Met
    770


<210> SEQ ID NO 4
<211> LENGTH: 749
<212> TYPE: PRT
<213> ORGANISM: Mus musculus

<400> SEQUENCE: 4

Met Ser Gln Trp Asn Gln Val Gln Gln Leu Glu Ile Lys Phe Leu Glu
  1               5                  10                  15

Gln Val Asp Gln Phe Tyr Asp Asp Asn Phe Pro Met Glu Ile Arg His
             20                  25                  30

Leu Leu Ala Gln Trp Ile Glu Thr Gln Asp Trp Glu Val Ala Ser Asn
         35                  40                  45

Asn Glu Thr Met Ala Thr Ile Leu Leu Gln Asn Leu Leu Ile Gln Leu
     50                  55                  60

Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                 85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Ile Gln Gly Pro Leu Glu
```

-continued

```
        115                 120                 125

Lys Ser Leu Gln Ser Ser Ser Val Ser Glu Arg Gln Arg Asn Val Glu
    130                 135                 140

His Lys Val Ser Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Gly Asp Lys Asn Ser Ile Leu Val Asn
            180                 185                 190

Gln Glu Val Leu Thr Leu Leu Gln Glu Met Leu Asn Ser Leu Asp Phe
        195                 200                 205

Lys Arg Lys Glu Ala Leu Ser Lys Met Thr Gln Ile Val Asn Glu Thr
    210                 215                 220

Asp Leu Leu Met Asn Ser Met Leu Leu Glu Glu Leu Gln Asp Trp Lys
225                 230                 235                 240

Lys Arg Gln Gln Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
            260                 265                 270

Leu Arg Gln Gln Leu Glu Lys Leu Gln Glu Gln Ser Thr Lys Met Thr
        275                 280                 285

Tyr Glu Gly Asp Pro Ile Pro Ala Gln Arg Ala His Leu Leu Glu Arg
    290                 295                 300

Ala Thr Phe Leu Ile Tyr Asn Leu Phe Lys Asn Ser Phe Val Val Glu
305                 310                 315                 320

Arg Gln Pro Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
            340                 345                 350

Glu Leu Asn Tyr Gln Val Lys Val Lys Ala Ser Ile Asp Lys Asn Val
        355                 360                 365

Ser Thr Leu Ser Asn Arg Arg Phe Val Leu Cys Gly Thr His Val Lys
    370                 375                 380

Ala Met Ser Ser Glu Glu Ser Ser Asn Gly Ser Leu Ser Val Glu Phe
385                 390                 395                 400

Arg His Leu Gln Pro Lys Glu Met Lys Cys Ser Thr Gly Ser Lys Gly
                405                 410                 415

Asn Glu Gly Cys His Met Val Thr Glu Glu Leu His Ser Ile Thr Phe
            420                 425                 430

Glu Thr Gln Ile Cys Leu Tyr Gly Leu Thr Ile Asn Leu Glu Thr Ser
        435                 440                 445

Ser Leu Pro Val Val Met Ile Ser Asn Val Ser Gln Leu Pro Asn Ala
    450                 455                 460

Trp Ala Ser Ile Ile Trp Tyr Asn Val Ser Thr Asn Asp Ser Gln Asn
465                 470                 475                 480

Leu Val Phe Phe Asn Asn Pro Pro Ser Val Thr Leu Gly Gln Leu Leu
                485                 490                 495

Glu Val Met Ser Trp Gln Phe Ser Ser Tyr Val Gly Arg Gly Leu Asn
            500                 505                 510

Ser Glu Gln Leu Asn Met Leu Ala Glu Lys Leu Thr Val Gln Ser Asn
        515                 520                 525

Tyr Asn Asp Gly His Leu Thr Trp Ala Lys Phe Cys Lys Glu His Leu
    530                 535                 540
```

-continued

```
Pro Gly Lys Thr Phe Thr Phe Trp Thr Trp Leu Glu Ala Ile Leu Asp
545                 550                 555                 560

Leu Ile Lys Lys His Ile Leu Pro Leu Trp Ile Asp Gly Tyr Ile Met
                565                 570                 575

Gly Phe Val Ser Lys Glu Lys Glu Arg Leu Leu Leu Lys Asp Lys Met
            580                 585                 590

Pro Gly Thr Phe Leu Leu Arg Phe Ser Glu Ser His Leu Gly Gly Ile
        595                 600                 605

Thr Phe Thr Trp Val Asp Gln Ser Glu Asn Gly Glu Val Arg Phe His
    610                 615                 620

Ser Val Glu Pro Tyr Asn Lys Gly Arg Leu Ser Ala Leu Ala Phe Ala
625                 630                 635                 640

Asp Ile Leu Arg Asp Tyr Lys Val Ile Met Ala Glu Asn Ile Pro Glu
                645                 650                 655

Asn Pro Leu Lys Tyr Leu Tyr Pro Asp Ile Pro Lys Asp Lys Ala Phe
            660                 665                 670

Gly Lys His Tyr Ser Ser Gln Pro Cys Glu Val Ser Arg Pro Thr Glu
        675                 680                 685

Arg Gly Asp Lys Gly Tyr Val Pro Ser Val Phe Ile Pro Ile Ser Thr
    690                 695                 700

Ile Arg Ser Asp Ser Thr Glu Pro Gln Ser Pro Ser Asp Leu Leu Pro
705                 710                 715                 720

Met Ser Pro Ser Ala Tyr Ala Val Leu Arg Glu Asn Leu Ser Pro Thr
                725                 730                 735

Thr Ile Glu Thr Ala Met Asn Ser Pro Tyr Ser Ala Glu
            740                 745


<210> SEQ ID NO 5
<211> LENGTH: 770
<212> TYPE: PRT
<213> ORGANISM: Mus musculus

<400> SEQUENCE: 5

Met Ala Gln Trp Asn Gln Leu Gln Gln Leu Asp Thr Arg Tyr Leu Lys
  1               5                  10                  15

Gln Leu His Gln Leu Tyr Ser Asp Thr Phe Pro Met Glu Leu Arg Gln
             20                  25                  30

Phe Leu Ala Pro Trp Ile Glu Ser Gln Asp Trp Ala Tyr Ala Ala Ser
         35                  40                  45

Lys Glu Ser His Ala Thr Leu Val Phe His Asn Leu Leu Gly Glu Ile
     50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
```

-continued

```
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Pro Glu Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590
```

-continued

```
Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Cys Thr Cys Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Asp Leu Thr Ser Glu Cys Ala Thr Ser
        755                 760                 765

Pro Met
    770


<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 6

gctataagat catggattgt acctgcatcc tggtgtctcc                            40


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Reagent

<400> SEQUENCE: 7

dgatttcccg taaatcat                                                    18


<210> SEQ ID NO 8
<211> LENGTH: 750
<212> TYPE: PRT
<213> ORGANISM: Homo sapiens

<400> SEQUENCE: 8

Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
```

-continued

```
     50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
    210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480
```

-continued

```
Pro Arg Asn Leu Ser Phe Phe Leu Thr Pro Pro Cys Ala Arg Trp Ala
            485                 490                 495

Gln Leu Ser Glu Val Leu Ser Trp Gln Phe Ser Ser Val Thr Lys Arg
        500                 505                 510

Gly Leu Asn Val Asp Gln Leu Asn Met Leu Gly Glu Lys Leu Leu Gly
    515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
        580                 585                 590

Asp Gln Gln Pro Gly Thr Phe Leu Leu Arg Phe Ser Glu Ser Ser Arg
    595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Cys
            645                 650                 655

Glu Cys Ile Pro Glu Asn Pro Leu Lys Tyr Leu Tyr Pro Asn Ile Asp
        660                 665                 670

Lys Asp His Ala Phe Gly Lys Tyr Tyr Ser Arg Pro Lys Glu Ala Pro
    675                 680                 685

Glu Pro Met Glu Leu Asp Gly Pro Lys Gly Thr Gly Tyr Ile Lys Thr
690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
        740                 745                 750
```

<210> SEQ ID NO 9
<211> LENGTH: 2869
<212> TYPE: DNA
<213> ORGANISM: Mus musculus

<400> SEQUENCE: 9

```
gccgcgacca gccaggccgg ccagtcgggc tcagcccgga gacagtcgag acccctgact      60

gcagcaggat ggctcagtgg aaccagctgc agcagctgga cacacgctac ctgaagcagc     120

tgcaccagct gtacagcgac acgttcccca tggagctgcg gcagttcctg gcaccttgga     180

ttgagagtca agactgggca tatgcagcca gcaaagagtc acatgccacg ttggtgtttc     240

ataatctctt gggtgaaatt gaccagcaat atagccgatt cctgcaagag tccaatgtcc     300

tctatcagca caaccttcga agaatcaagc agtttctgca gagcaggtat cttgagaagc     360

caatggaaat tgcccggatc gtggcccgat gcctgtggga agagtctcgc ctcctccaga     420

cggcagccac ggcagcccag caagggggcc aggccaacca cccaacagcc gccgtagtga     480

cagagaagca gcagatgttg gagcagcatc ttcaggatgt ccggaagcga gtgcaggatc     540

tagaacagaa aatgaaggtg gtggagaacc tccaggacga ctttgatttc aactacaaaa     600
```

-continued

```
ccctcaagag ccaaggagac atgcaggatc tgaatggaaa caaccagtct gtgaccagac    660
agaagatgca gcagctggaa cagatgctca cagccctgga ccagatgcgg agaagcattg    720
tgagtgagct ggcggggctc ttgtcagcaa tggagtacgt gcagaagaca ctgactgatg    780
aagagctggc tgactggaag aggcggccag agatcgcgtg catcggaggc cctcccaaca    840
tctgcctgga ccgtctggaa aactggataa cttcattagc agaatctcaa cttcagaccc    900
gccaacaaat taagaaactg gaggagctgc agcagaaagt gtcctacaag ggcgacccta    960
tcgtgcagca ccggcccatg ctggaggaga ggatcgtgga gctgttcaga aacttaatga   1020
agagtgcctt cgtggtggag cggcagccct gcatgcccat gcacccggac cggcccttag   1080
tcatcaagac tggtgtccag tttaccacga aagtcaggtt gctggtcaaa tttcctgagt   1140
tgaattatca gcttaaaatt aaagtgtgca ttgataaaga ctctggggat gttgctgccc   1200
tcagagggtc tcggaaattt aacattctgg gcacgaacac aaaagtgatg aacatggagg   1260
agtctaacaa cggcagcctg tctgcagagt tcaagcacct gacccttagg gagcagagat   1320
gtgggaatgg aggccgtgcc aattgtgatg cctccttgat cgtgactgag gagctgcacc   1380
tgatcacctt cgagactgag gtgtaccacc aaggcctcaa gattgaccta gagacccact   1440
ccttgccagt tgtggtgatc tccaacatct gtcagatgcc aaatgcttgg gcatcaatcc   1500
tgtggtataa catgctgacc aataacccca agaacgtgaa cttcttcact aagccgccaa   1560
ttggaacctg ggaccaagtg gccgaggtgc tcagctggca gttctcgtcc accaccaagc   1620
gagggctgag catcgagcag ctgacaacgc tggctgagaa gctcctaggg cctggtgtga   1680
actactcagg gtgtcagatc acatgggcta aattctgcaa agaaaacatg gctggcaagg   1740
gcttctcctt ctgggtctgg ctagacaata tcatcgacct tgtgaaaaag tatatcttgg   1800
ccctttggaa tgaagggtac atcatgggtt tcatcagcaa ggagcgggag cgggccatcc   1860
taagcacaaa gcccccgggc accttcctac tgcgcttcag cgagagcagc aaagaaggag   1920
gggtcacttt cacttgggtg gaaaaggaca tcagtggcaa gacccagatc cagtctgtag   1980
agccatacac caagcagcag ctgaacaaca tgtcatttgc tgaaatcatc atgggctata   2040
agatcatgga ttgtacctgc atcctggtgt ctccacttgt ctacctctac cccgacattc   2100
ccaaggagga ggcatttgga aagtactgta ggcccgagag ccaggagcac cccgaagccg   2160
acccaggtag tgctgccccg tacctgaaga ccaagttcat ctgtgtgaca ccaacgacct   2220
gcagcaatac cattgacctg ccgatgtccc cccgcacttt agattcattg atgcagtttg   2280
gaaataacgg tgaaggtgct gagccctcag caggagggca gtttgagtcg ctcacgtttg   2340
acatggatct gacctcggag tgtgctacct cccccatgtg aggagctgaa accagaagct   2400
gcagagacgt gacttgagac acctgccccg tgctccaccc ctaagcagcc gaaccccata   2460
tcgtctgaaa ctcctaactt tgtggttcca gatttttttt tttaatttcc tacttctgct   2520
atctttgggc aatctgggca ctttttaaaa gagagaaatg agtgagtgtg ggtgataaac   2580
tgttatgtaa agaggagaga cctctgagtc tggggatggg gctgagagca gaagggaggc   2640
aaaggggaac acctcctgtc ctgcccgcct gccctccttt ttcagcagct cgggggttgg   2700
ttgttagaca agtgcctcct ggtgcccatg gctacctgtt gccccactct gtgagctgat   2760
accccattct gggaactcct ggctctgcac tttcaacctt gctaatatcc acatagaagc   2820
taggactaag cccaggaggt tcctctttaa attaaaaaaa aaaaaaaaa              2869
```

<210> SEQ ID NO 10

-continued

<211> LENGTH: 3943
<212> TYPE: DNA
<213> ORGANISM: Homo sapiens

<400> SEQUENCE: 10
attaaacctc tcgccgagcc cctccgcaga ctctgcgccg gaaagtttca tttgctgtat 60
gccatcctcg agagctgtct aggttaacgt tcgcactctg tgtatataac ctcgacagtc 120
ttggcaccta acgtgctgtg cgtagctgct cctttggttg aatccccagg cccttgttgg 180
ggcacaaggt ggcaggatgt ctcagtggta cgaacttcag cagcttgact caaaattcct 240
ggagcaggtt caccagcttt atgatgacag ttttcccatg gaaatcagac agtacctggc 300
acagtggtta gaaaagcaag actgggagca cgctgccaat gatgtttcat ttgccaccat 360
ccgttttcat gacctcctgt cacagctgga tgatcaatat agtcgctttt ctttggagaa 420
taacttcttg ctacagcata acataaggaa aagcaagcgt aatcttcagg ataattttca 480
ggaagaccca atccagatgt ctatgatcat ttacagctgt ctgaaggaag aaaggaaaat 540
tctggaaaac gcccagagat ttaatcaggc tcagtcgggg aatattcaga gcacagtgat 600
gttagacaaa cagaaagagc ttgacagtaa agtcagaaat gtgaaggaca aggttatgtg 660
tatagagcat gaaatcaaga gcctggaaga tttacaagat gaatatgact tcaaatgcaa 720
aaccttgcag aacagagaac acgagaccaa tggtgtggca aagagtgatc agaaacaaga 780
acagctgtta ctcaagaaga tgtatttaat gcttgacaat aagagaaagg aagtagttca 840
caaaataata gagttgctga atgtcactga acttacccag aatgccctga ttaatgatga 900
actagtggag tggaagcgga gacagcagag cgcctgtatt ggggggccgc ccaatgcttg 960
cttggatcag ctgcagaact ggttcactat agttgcggag agtctgcagc aagttcggca 1020
gcagcttaaa aagttggagg aattggaaca gaaatacacc tacgaacatg accctatcac 1080
aaaaaacaaa caagtgttat gggaccgcac cttcagtctt ttccagcagc tcattcagag 1140
ctcgtttgtg gtggaaagac agccctgcat gccaacgcac cctcagaggc cgctggtctt 1200
gaagacaggg gtccagttca ctgtgaagtt gagactgttg gtgaaattgc aagagctgaa 1260
ttataatttg aaagtcaaag tcttatttga taaagatgtg aatgagagaa atacagtaaa 1320
aggatttagg aagttcaaca ttttgggcac gcacacaaaa gtgatgaaca tggaggagtc 1380
caccaatggc agtctggcgg ctgaatttcg gcacctgcaa ttgaaagaac agaaaaatgc 1440
tggcaccaga acgaatgagg gtcctctcat cgttactgaa gagcttcact cccttagttt 1500
tgaaacccaa ttgtgccagc ctggtttggt aattgacctc gagacgacct ctctgcccgt 1560
tgtggtgatc tccaacgtca gccagctccc gagcggttgg gcctccatcc tttggtacaa 1620
catgctggtg gcggaaccca ggaatctgtc cttcttcctg actccaccat gtgcacgatg 1680
ggctcagctt tcagaagtgc tgagttggca gttttcttct gtcaccaaaa gaggtctcaa 1740
tgtggaccag ctgaacatgt tgggagagaa gcttcttggt cctaacgcca gccccgatgg 1800
tctcattccg tggacgaggt tttgtaagga aaatataaat gataaaaatt ttcccttctg 1860
gctttggatt gaaagcatcc tagaactcat taaaaaacac ctgctccctc tctggaatga 1920
tgggtgcatc atgggcttca tcagcaagga gcgagagcgt gccctgttga aggaccagca 1980
gccggggacc ttcctgctgc ggttcagtga gagctcccgg gaaggggcca tcacattcac 2040
atgggtggag cggtcccaga acggaggcga acctgacttc catgcggttg aaccctacac 2100
gaagaaagaa ctttctgctg ttactttccc tgacatcatt cgcaattaca aagtcatggc 2160
ttgtgagtgt attcctgaga atcccctgaa gtatctgtat ccaaatattg acaaagacca 2220

-continued

```
tgcctttgga aagtattact ccaggccaaa ggaagcacca gagccaatgg aacttgatgg   2280

ccctaaagga actggatata tcaagactga gttgatttct gtgtctgaag ttcacccttc   2340

tagacttcag accacagaca acctgctccc catgtctcct gaggagtttg acgaggtgtc   2400

tcggatagtg ggctctgtag aattcgacag tatgatgaac acagtataga gcatgaattt   2460

ttttcatctt ctctggcgac agttttcctt ctcatctgtg attccctcct gctactctgt   2520

tccttcacat cctgtgtttc tagggaaatg aaagaaaggc cagcaaattc gctgcaacct   2580

gttgatagca agtgaatttt tctctaactc agaaacatca gttactctga agggcatcat   2640

gcatcttact gaaggtaaaa ttgaaaggca ttctctgaag agtgggtttc acaagtgaaa   2700

aacatccaga tacacccaaa gtatcaggac gagaatgagg gtcctttggg aaaggagaag   2760

ttaagcaaca tctagcaaat gttatgcata aagtcagtgc ccaactgtta taggttgttg   2820

gataaatcag tggttattta gggaactgct tgacgtagga acggtaaatt tctgtgggag   2880

aattcttaca tgttttcttt gctttaagtg taactggcag ttttccattg gtttacctgt   2940

gaaatagttc aaagccaagt ttatatacaa ttatatcagt cctctttcaa aggtagccat   3000

catggatctg gtagggggaa aatgtgtatt ttattacatc tttcacattg gctatttaaa   3060

gacaaagaca aattctgttt cttgagaaga gaacatttcc aaattcacaa gttgtgtttg   3120

atatccaaag ctgaatacat tctgctttca tcttggtcac atacaattat ttttacagtt   3180

ctcccaaggg agttaggcta ttcacaacca ctcattcaaa agttgaaatt aaccatagat   3240

gtagataaac tcagaaattt aattcatgtt tcttaaatgg gctactttgt cctttttgtt   3300

attagggtgg tatttagtct attagccaca aaattgggaa aggagtagaa aaagcagtaa   3360

ctgacaactt gaataataca ccagagataa tatgagaatc agatcatttc aaaactcatt   3420

tcctatgtaa ctgcattgag aactgcatat gtttcgctga tatatgtgtt tttcacattt   3480

gcgaatggtt ccattctctc tcctgtactt tttccagaca cttttttgag tggatgatgt   3540

ttcgtgaagt atactgtatt tttacctttt tccttcctta tcactgacac aaaaagtaga   3600

ttaagagatg ggtttgacaa ggttcttccc ttttacatac tgctgtctat gtggctgtat   3660

cttgtttttc cactactgct accacaacta tattatcatg caaatgctgt attcttcttt   3720

ggtggagata aagatttctt gagttttgtt ttaaaattaa agctaaagta tctgtattgc   3780

attaaatata atatcgacac agtgctttcc gtggcactgc atacaatctg aggcctcctc   3840

tctcagtttt tatatagatg gcgagaacct aagtttcagt tgattttaca attgaaatga   3900

ctaaaaaaca aagaagacaa cattaaaaac aatattgttt cta                     3943
```